(12) United States Patent
Weinstein

(10) Patent No.: US 6,291,642 B1
(45) Date of Patent: Sep. 18, 2001

(54) MAMMALIAN CELL CYCLE PROTEIN

(75) Inventor: Jasminder Weinstein, Westlake Village, CA (US)

(73) Assignees: Amgen Inc., Thousands Oaks; The Regents of the University of California, Oakland, both of CA (US)

( * ) Notice: Subject to any disclaimer, the term of this patent is extended or adjusted under 35 U.S.C. 154(b) by 0 days.

(21) Appl. No.: 08/988,856

(22) Filed: Dec. 11, 1997

Related U.S. Application Data

(60) Continuation of application No. 08/448,864, filed on May 24, 1995, now abandoned, which is a division of application No. 08/195,730, filed on Feb. 14, 1994, now abandoned.

(51) Int. Cl.[7] .................................................. C07K 14/435
(52) U.S. Cl. ............................................ 530/350; 435/69.1
(58) Field of Search ............................ 435/69.1; 530/350

(56) References Cited

PUBLICATIONS

Blacketer et al., Molecular and Cell. Biol. 13, 5567–5581 (1993).
Healy et al., Molecular and Cell. Biol. 11, 5767–5780 (1991).
Mayer–Kaekel et al., Cell 72, 621–633 (1993).
Zolnierowicz et al., The FASEB Journal 5, A832 (1991).
Amon et al., Yeast 8, S314 (1992).
Andersson et al., Nature 278, 364–365 (1979).
Beach et al., Nature 300, 706–709 (1982).
Brizuela et al., Proc. Natl. Acad. Sci. USA 86, 4362–4366 (1989).
Byers et al., Cold Spring Harbor Symp. Quant. Biol. 38, 123–131 (1974).
Choi et al., Biochem. Biophys. Res. Comm. 172, 1324–1330 (1990).
Chomczynski et al., Anal. Biochem. 162, 156–159 (1987).
Choo et al., DNA 5, 529–537 (1986).
Clark–Lewis et al., J. Biol. Chem. 266, 15180–15184 (1991).
Crews et al., Cell Growth Diff. 3, 135–142 (1992).
Dalrymple et al., Cell 58, 811–812 (1989).
Deng et al., Cell 71, 791–801 (1992).
Devoto et al., Cell 68, 167–176 (1992).
Dowdy et al., Cell 73, 499–511 (1993).
Draetta et al., Cell 50, 319–325 (1987).
Draetta et al., Cell 54, 17–26 (1988).
Draetta, Trends Biochem. Sci. 15, 378–383 (1990).
Dulic et al., Science 257, 1958–1961 (1992).
Dunphy et al, Cell 55, 925–928 (1988).
Dutcher et al., Genetics 100, 175–184 (1982).
Dynlacht et al., Nature 363, 176–179 (1993).
Erickson et al., J. Biol. Chem 265, 19728–19735 (1990).
Ewen et al., Science 255, 85–87 (1992).
Ewen et al., Cell 73, 487–497 (1993).
Fang et al., Cell 66, 731–742 (1991).

Fong et al., Proc. Natl. Acad. Sci. USA 83, 2162–2166 (1986).
Gautieir et al., Cell 54, 433–439 (1988).
Girling et al., Nature 362, 83–87 (1993).
Goebl et al., Trends Biochem. Sci. 16, 173–177 (1991).
Hanks et al., 241, 42–52 (1988).
Hartwell et al., Genetics 110, 381–395 (1985).
Hartwell, J. Bacteriology 115, 966–974 (1973).
Hartwell et al., Science 183, 46–51 (1974).
Heintz et al., Mol. Cell. Biol. 3, 539–550 (1983).
Hoffman et al., EMBO J. 12, 53–63 (1993).
Kaelin et al., Cell 70, 351–364 (1992).
Kochanski et al., J. Cell Biol. 110, 1599–1605 (1990).
Koff et al., Science 257, 1689–1694 (1992).
Labbe et al., Cell 57, 253–263 (1989).
Langan et al., Mol. Cell. Biol. 9, 3860–3868 (1989).
Lee et al., Nature 327, 27–35 (1987).
Letwin et al., EMBO J. 11, 3521–3531 (1992).
Lew et al., Cell 66, 1197–1206 (1991).
Maniotis, et al., Cell 67, 495–504 (1991).
Matsushime et al., Cell 71, 323–334 (1992).
Mazia, Int. Rev. Cytol. 100, 49–92 (1987).
Meyerson et al., EMBO J. 11, 2909–2917 (1992).
Molz et al., EMBO J. 12, 1723–1732 (1993).
Nevins Sience 258, 424–429 (1992).
Nurse, Nature 344, 503–508 (1990).
O'Farrell, Trends Cell. Biol 2, 159–163 (1992).
Osmani et al., Cell 53, 237–244 (1988).
Osmani et al., EMBO J. 10, 2669–2679 (1991).
Osmani et al., Cell 67, 283–291 (1991).
Palmer et al., J. Cell. Biol. 109, 3355–3366 (1989).
Paulson et al., J. Biol. Chem. 264, 17615–17618 (1989).
Petersen–Bijorn et al., Mol. Cell. Biol. 9, 3698–3709 (1989).
Pines et al., Cell 58, 833–846 (1989).
Pines, Sci. 18, 195–197 (1993).
Rovera et al., Proc. Natl. Acad. Sci. USA 76, 2779–2783 (1979).
Ruggieri et al., Proc. Natl. Acad. Sci. USA 86, 8778–8782 (1989).
Sambrook et al., Molecular Cloning. A Laboratory Manual. Second Edition (1989), pp. 9.52–9.55.
Schweitzer et al., Yeast 7, 265–273 (1991).
Sethi et al., Mol. Cell. Biol. 11, 5592–5602 (1991).
Shaw et al., Mol. Gen. Genet 218, 453–459 (1989).
Sherr, Cell 73, 1059–1065 (1993).

(List continued on next page.)

*Primary Examiner*—Marianne P. Allen
(74) *Attorney, Agent, or Firm*—Finnegan Henderson Farabow Garrett & Dunner, LLP

(57) ABSTRACT

A novel mammalian cell cycle protein, p55CDC, DNA sequences encoding p55CDC, and a method for producing the protein are described. Also described are methods for detecting p55CDC and methods for modulating cell division by compounds which control the level or activity of p55CDC or p55CDC-associated protein complexes.

7 Claims, 18 Drawing Sheets

OTHER PUBLICATIONS

Simchen et al., Genetics 86, 57–72 (1977).
Spevak et al., Mol. Cell. Biol. 13, 4953–4966 (1993).
Turner et al., Blood 80, 374–381 (1992).
Vallen et al., Cell 69, 505–515 (1993).
Van der Voorn et al., FEBS Lett. 307, 131–134 (1992).
Weinstein et al., J. Biol. Chem. 262, 17735–17743 (1987).
Winey et al., The Centrosome. V. Kalnius ed. (Orlando: Academic Press) 201–222 (1992).
Wittenberg et al., Mol. Cell. Biol. 9, 4064–4068 (1989).
Yochem et al., J. Bol. Biol. 195, 233–245 (1987).
Zhang et al., Gene 97, 153–161 (1991).
Engels et al., Angew. Chem. Intl. 28, 716–734 (1989).

```
                                                            A           A G T
                   A             TC           A A   G G T T      C                                         A G         T
553 AACGGTTTTGATGTGGAGGAAGCCAAGATCCTCAGGCTCAGTGGAAAACCTCAGAGGCTACCAGAAGGCTACACCAGAAGACAGATTGAAAGTACTCTACAGCCAAGAAGCCACGGCCTGGCTCC 160
    N  G  F  D  V  E  E  A  K  I  L  R  L  S  G  K  P  Q  N  A  P  E  G  Y  Q  N  R  L  K  V  L  Y  S  Q  K  A  T  P  G  S

C          AC   CT            CT C G      G           A           T       C           G           T      G        C G C
673 AGTCGGAAGGCTTGCAGATACATTCCTTCCCTGCCAGAGACAGGATTCTTGATGCCCCTGAAATCCGGAATGACTACTACCTGAATCTTGTGGATTGGAGCTCTGGAAATGTGTATTAGCTGTG 200
    S  R  K  A  C  R  Y  I  P  S  L  P  D  R  I  L  D  A  P  E  I  R  N  D  Y  Y  L  N  L  V  D  W  S  S  G  N  V  L  A  V
                    T

C G      GT AA C T                                             A T    C  T
793 GCACTGGACAACAGTGTGTACTTATGGAACGCTGGTTCCGGTGACATCCTGCAGCTGTTGCAAATGGAGCAGCCTGGGGACTACATATCATCCGTGGCCTGGATCAAAGAGGGCAACTAC 240
    A  L  D  N  S  V  Y  L  W  N  A  G  S  G  D  I  L  Q  L  L  Q  M  E  Q  P  G  D  Y  I  S  S  V  A  W  I  K  E  G  N  Y
                   S                     S                                       E

T          C G                                                           T         T        C      GG        A C
913 CTGGCTGTGGGCACCAGTAATGCTGAGGTGCAGCTGTGGGATGTGCAGCAGAAACGGCTTCGAAACATGACCAGCCACTCTGCTCGAGTAAGCTCCCTGAGTTGGAACAGCTATATC 280
    L  A  V  G  T  S  N  A  E  V  Q  L  W  D  V  Q  Q  K  R  L  R  N  M  T  S  H  S  A  R  V  S  S  L  S  W  N  S  Y  I
                                                                                G
```

Fig. 2C

```
                C                  T             G                     C              C        G
1033 CTGTCAAGTGGTTCACGGATCTGGCCACATCCACGACGATGTTCGAGTAGAGAACACCATGGCCACACTGAGTGGCCATAGCCAGGAAGTATGTGGCTGCGCTGGGCCCAGAT
      L  S  S  G  S  R  S  G  H  I  H  H  D  V  R  V  A  E  H  H  V  A  T  L  S  G  H  S  Q  E  V  C  G  L  R  W  A  P  D  320

T         C  T       T  G                GG                                                      C          G
1153 GGACGACATCTGGCAAGCGGTGGCAATGATAACATTGTCAACGTGTGGGCCTAGTGGTCCTGGAGAAAGTGGCTGGGTCCCCTGCAGACATTCACTCAACATCAAGGTGTGTCAAGGCT
      G  R  H  L  A  S  G  G  N  D  N  I  V  N  V  W  P  S  G  P  G  E  S  G  W  V  P  L  Q  T  F  T  Q  H  Q  G  A  V  K  A  360
                                               A  G

A              G                             GC           C        T G       G                          C     CC
1273 GTTGCATGGTGTCCCTGGCAGTCCAATATCCTGGCAACAGTGACCGACAGGTACCAGTGGGTACGGTGGCACCAGTCTGATGACGACCTGTCTCTGGAGCCTGTCTGAGTGCTGTGGAATGTGCATTCC
      V  A  W  C  P  W  Q  S  N  I  L  A  T  G  G  T  S  D  R  H  I  R  I  W  N  V  C  S  G  A  C  L  S  A  V  D  V  H  S  400
                    V                                                                                                 A

T  C                    A                       A            A                                   T A
1393 CAGGTGTGCTCCATCCTCTGGTCTCCCACTATAAGGAGCTCATCTCAGGCCATGGGTTTGCCCAGAACCAGCTGGTTATTTGAAGTACCAACCATGGCCAAGGTGGCAGAGCTCAAA
      Q  V  C  S  I  L  W  S  P  H  Y  K  E  L  I  S  G  H  G  F  A  Q  N  Q  L  V  I  W  K  Y  P  T  M  A  K  V  A  E  L  K  440
```

Fig. 2D

1513 GGTCACACAGCCCGGTCCTGAGTCTCACCATGAGTCCAGAGGGCCACAGTGGCATCTGCAGCAGCCGATGAGACTCTGCGGCTCTGGCGCTGCTTGAGCTGGACCCTGCCCTTCGG
         G  H  T  A  R  V  L  S  L  T  M  S  P  D  G  A  T  V  A  S  A  A  A  D  E  T  L  R  L  W  R  C  F  E  L  D  P  A  L  R   480
                           S                                                                                                R

1633 CGGGAGCGGGAAAAAGCCAGCACATCTAAAAGTAGCCTCATCCACCAGGCATCCGGTGAAAGACAACCCTTTCTTTTCCCTTCTTGATTTTGTTGTTGTTTATTTTTTCTAATAAAGT
         R  E  R  E  K  A  S  T  S  K  S  S  L  I  H  Q  G  I  R  *                                                          500
                           A  A

1753 TCATATCTTCCTTTC

Fig. 3A

```
IPSLPDRILD  APEIRNDYYLNLVDWS            SGNVLAVAL  DNSVYLWN  (168-210)
AGS GD ILQLLQMEQPGDYISS      VAWI       KEGNYLAVGT SNAEVQLWD (211-254)
VQ  QQKRLR  NMTSHSARVSS      LSW        NSYILSSGSR S GHIHHHD (255-294)
VRVAE HHV   ATLSGHSQEVCG     LRWAP      DCRHLASGGN DNIVNVWP  (295-336)
SGPGESGWVPLQTFTQHGAVKA       VAWCPWQSNI LATGGGTSDRHIRIWN     (337-386)
VCSGAC LSA  VDVHSQ VCS       ILWSP      HYKELISGHGFAQNQLVIWK (387-429)
YPIMAK  V AE LKGHTARVLS      LTMSP      DCATVASAA  ADETLRLWR (430-471)
```

Fig. 3B

Fig. 3C p55CDC Antibody

MAMMALIAN CELL CYCLE PROTEIN

This is a continuing application of U.S. Ser. No. 08/448,864 filed May 24, 1995, now abandoned which is a division of U.S. Ser. No. 08/195,730 filed Feb. 14, 1994 no abandoned.

BACKGROUND OF THE INVENTION

The invention relates to a mammalian cell cycle protein, p55CDC, DNA sequences encoding same, antibodies specific for the protein, a method for producing the protein and methods for modulating cell division by controlling the levels or activity of p55CDC or p55CDC-associated protein complexes.

BACKGROUND OF THE INVENTION

The eukaryotic cell cycle has a growth phase and a reproductive phase, the latter composed of the chromosome cycle and the centrosome cycle which intersect in the establishment of the mitotic apparatus (for review, see 47). The profound morphologic changes which result in mitosis are accompanied by a cascade of phosphorylation and dephosphorylation events. In mammalian cells, different complexes of kinases and their associated regulatory proteins control progression through discrete steps of the cell cycle (for review, see 60,67). While all eukaryotic cells use similar mechanisms to regulate progression through the stages of the cell cycle, it is clear that unique combinations of regulatory cyclins, kinases and phosphatases are responsible for cell- and organism-specific patterns of cell division (18,51,52).

A variety of kinases have been identified which control the crucial transitions through the cell cycle. The most well characterized is the p34cdc2 protein, which has been identified in all eukaryotic cells which have been examined (3, 16, 20, 28, 40, 41, 42, 59, 76). In addition, many other kinases which have homology to p34cdc2 and, like p34cdc2 fluctuate in activity during the cell cycle, have been described (48,60). Other types of kinases have also been shown to vary in activity at different stages of the cell cycle, and have been proposed to play a role in control of cell division, although they share little or no homology with p34cdc2. These include the MAP kinases, and the MEK kinases which regulate MAP kinase activity (for review, see 11). In addition, a novel kinase has been identified in the fungus *Aspergillus nidulans*, the NIMA kinase, which is required to initiate mitosis (53–55). A mammalian kinase, Nek1, which has homology to the NIMA kinase, has been found in mouse, where it is expressed at high levels in gonadal tissues and may be required for meiosis (43).

As mentioned above, the activity of many of these kinases is regulated by their association with one or more cyclins. The cyclins are homologous with one another within a conserved region termed the cyclin box (44). The fluctuations in activity of the cyclin dependent kinases during the cell cycle result from differential association with newly synthesized cyclins, which are then degraded at specific transition points in the cell cycle. However, not all cyclins demonstrate the same degree of fluctuation during the cell cycle; for example, levels of the D type cyclins do not oscillate as dramatically during the cell cycle as the A and B type cyclins. In addition, a recently described cyclin, the mcs2 cyclin of *S. pombe*, shows no variation in level during the cell cycle, nor does the novel kinase activity associated with the mcs2 cyclin oscillate (49).

Experiments in yeast have defined a number of other cell division cycle (Cdc) proteins which are also crucial for the orderly progression of the cell cycle, although the functions of many of these proteins have not been precisely defined (34). Two of these proteins, the products of the CDC20 and CDC4 genes, have been proposed to be elements of the mitotic spindle or segregational apparatus (32). The cdc20 temperature sensitive mutants arrest in mitosis at the non-permissive temperature, after the formation of a complete short spindle and nuclear migration to the neck between the mother cell and a large bud (6). It has been proposed that the Cdc20 protein is directly required for chromosomal movement (56). In addition, the Cdc20 protein is required for modulation of microtubule structure, either by promoting microtubule disassembly (1,65) or by altering the surface of the microtubules, and is also required for microtubule-dependent processes other than mitosis (65).

The CDC4 gene of *S. cerevisiae* (33), is essential for the initiation of DNA synthesis. Cells carrying a conditional-lethal, temperature-sensitive mutation in cdc4 arrest division at the non-permissive temperature, and the cells have a termination phenotype of multiple buds, a single nucleus, and duplicated spindle pole bodies connected by a bridge structure (6). CDC4 also appears to be required for karyogamy and sporulation (21,68,71). While the mechanism of action of the Cdc4 protein is still unknown, subcellular localization studies in yeast have demonstrated that it is associated with the nucleoskeleton (7). The appearance of the duplicated spindle pole bodies has been proposed to indicate that the CDC4 gene product is required for separation of the bodies and formation of the completed spindle (6,75). It has recently been demonstrated that removal of the centrosome (the equivalent of the spindle pole body in higher eukaryotes) from mammalian cells uncouples the growth cycle from the reproductive cycle, indicating that cell division requires the presence of centrosomes to establish the bipolar mitotic spindle (45).

It is an object of the present invention to identify one or more proteins involved in regulation of the cell cycle, wherein said proteins may be targets for compounds which modulate the cell cycle. A novel protein, termed p55CDC has been identified. mRNA encoding p55CDC was ubiquitously present in all cell lines examined, as well as in embryonic tissue, placenta and adult hematopoietic tissues, but was not detected in cells induced to differentiate and cease cell division. The deduced amino acid sequence of human p55CDC demonstrates regions of homology with the *S. cerevisiae* Cdc20 and Cdc4 proteins within the Gβ-repeats found in the carboxy terminal half of these three proteins. Expression of p55CDC appears to be crucial for cell division in mammalian cells. p55CDC is phosphorylated in cycling cells. Immune complexes precipitated by a polyclonal antiserum to p55CDC have a kinase activity which fluctuates during the cell cycle, although p55CDC itself does not appear to be an endogenous substrate of the kinase activity.

SUMMARY OF THE INVENTION

The invention relates to a novel mammalian protein, p55CDC, which is essential for cell division. It has been found that p55CDC is expressed in actively proliferating cells while expression is not detected in slowly dividing or quiescent cells. Transfection of antisense p55CDC cDNA into CHO cells resulted in the isolation of only those cells having a compensatory increase in p55CDC mRNA having the sense orientation.

DNA sequences encoding biologically active p55CDC are also provided by the invention. DNA sequences include rat (SEQ. ID NO: 1) and human (SEQ. ID NO: 3) p55CDC and DNA hybridizing to rat or human p55CDC, or to a fragment thereof, wherein the hybridizing DNA encodes biologically active p55CDC. Also provided for are vectors containing p55CDC DNA sequences and host cells transformed or transfected with said vectors. A method of producing a p55CDC polypeptide comprising culturing transformed or transfected host cells such that p55CDC is expressed is also included p55CDC polypeptides of the invention will preferably form a complex with one or more host proteins such that the complex has cell-cycle dependent kinase activity. The kinase activity of p55CDC complexes will fluctuate during the cell cycle.

A method for modulating cell division is also encompassed by the invention, wherein the method comprises introducing into a cell (e.g. a tumor cell) a compound which modulates the kinase activity of p55CDC complexes. Modulation of p55CDC associated kinase activity may involve an increase or decrease in activity at certain periods during the cell cycle which in turn may lead to alterations in timing or specificity of p55CDC-associated kinase activity. In a preferred embodiment, cell division is inhibited by exposure to compounds which interfere with p55CDC complex formation.

(A) Total RNA (30 µg) from a variety of rat tissues at different developmental stages was probed with a rat genomic 0.26 kb Pst I fragment.

B) PolyA+ RNA (2.5 µg) from human tissues was probed with a [32P] labelled p55CDC cDNA from rat.

Figure 1A:
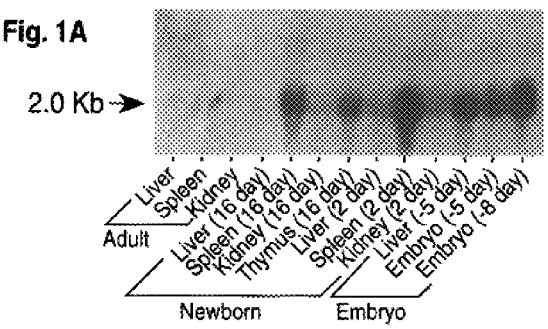
FIG. 1. Northern Analysis of p55CDC.
Figure 1B:
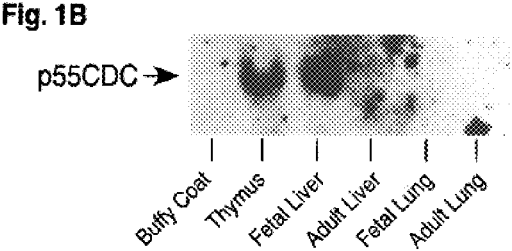

(C) PolyA+ RNA (2.5 µg) from human hematopoietic cell lines was analyzed with the same probe as in FIG. 1B. The signal obtained with a rat actin CDNA probe is shown for comparison.

(D) Total RNA 30 µg) prepared from cell lines that were induced to differentiate as described in Experimental Procedures and from control cells was probed with the same probe as in FIG. 1B. The ethidium bromide stain for 28SRNA is shown for comparison. All details for RNA isolation and Northern blot hybridization are described in Experimental Procedures.

Figure 2A:
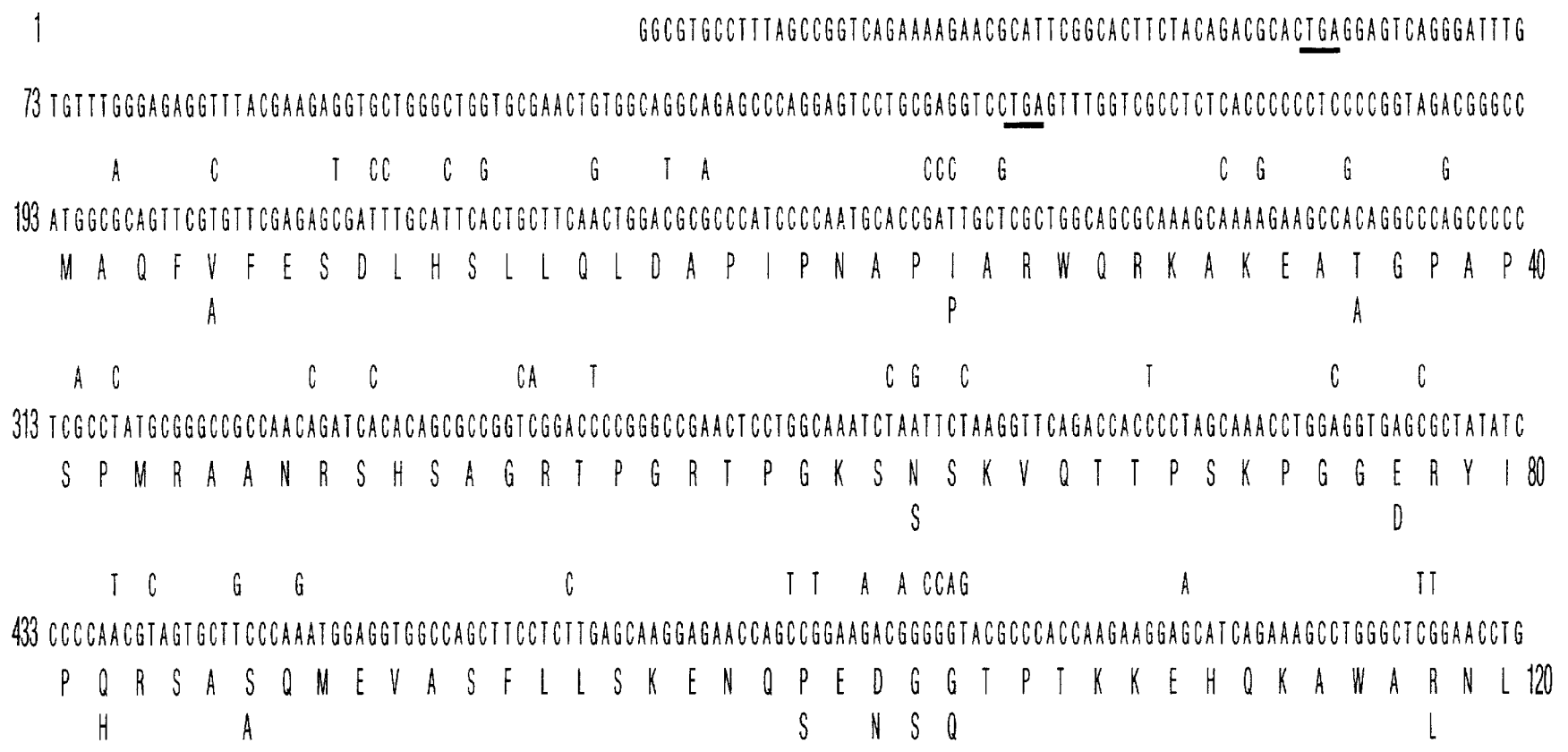

FIG. 2 Rat and Human p55CDC DNA sequence.

The compiled sequence from two rat cDNA clones is shown. The open reading frame of the human cDNA is shown only where it differs from the rat sequence. Nucleotide base pair numbers are shown to the left and amino acids, deduced from the nucleotides, are numbered at the right. Two in frame stop codons upstream of the initiation methionine are underlined and a polyadenylation signal downstream of the stop codon is boxed.

Figure 3B:
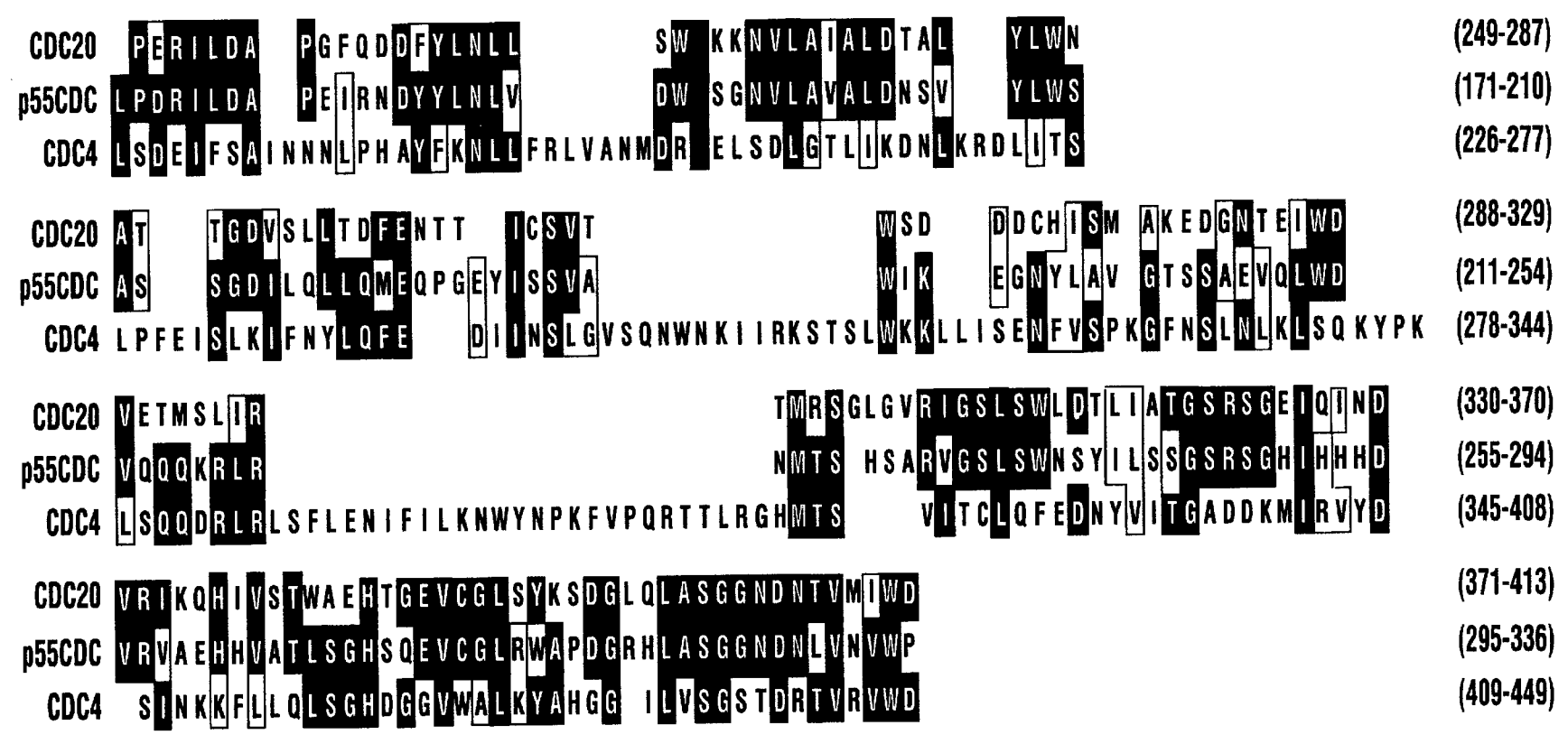
Figure 3C:
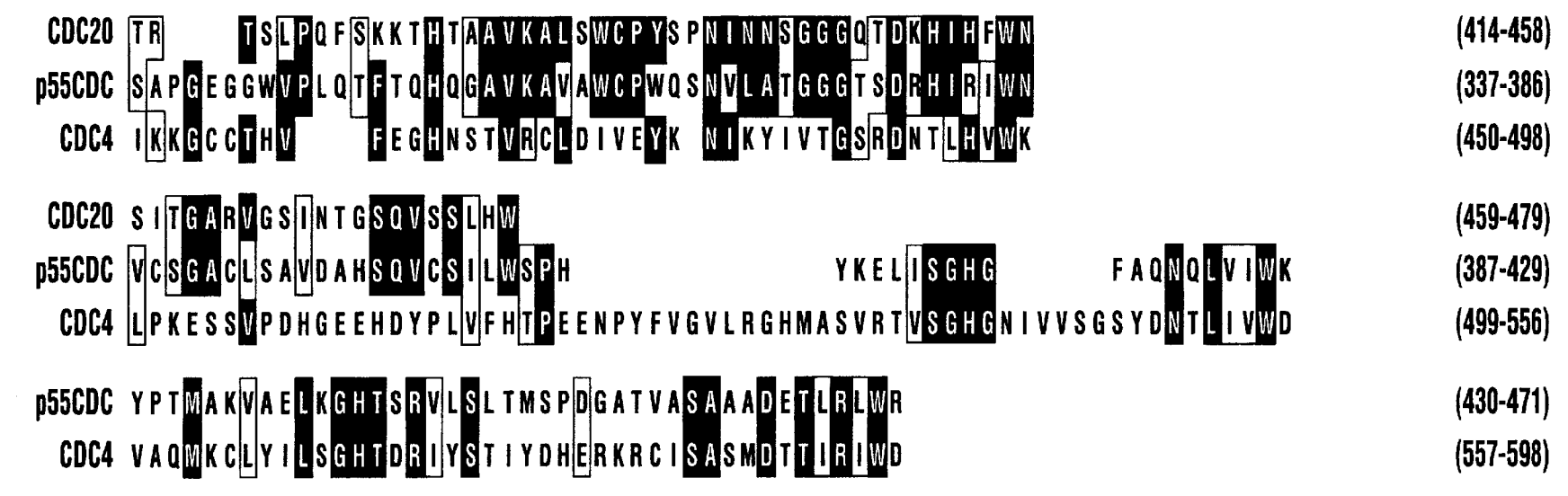

FIG. 3. p55CDC has seven Gβ-repeats and shows homology to the S. cerevisiae Cdc20 and Cdc4 proteins.

(A) The alignment of the seven rat p55CDC repeats was manually constructed following pairwise comparisons using the GCG BESTFIT program. Gaps were introduced to obtain optimal alignment and are represented by spaces. Identical or highly conserved residues which occur at a frequency of 4 times or greater are shown as white on black. Highly conservative substitutions are defined as Ile, Leu or Val, Ser or Thr, and Ala or Gly.

(B) Alignment of the β-repeats of human p55CDC with the Cdc20 and Cdc4 repeats was obtained using the GCG BESTFIT program followed by visual optimisation. Gaps were introduced to obtain optimal alignment and are represented by spaces. Identical residues are shown as white on black and the highly conserved residues are boxed. Highly conservative substitutions are defined as Ile, Leu or Val, Ser or Thr, Ala or Gly, Tyr or Phe, Asp or Glu and Arg, Lys or His.

Figure 4:
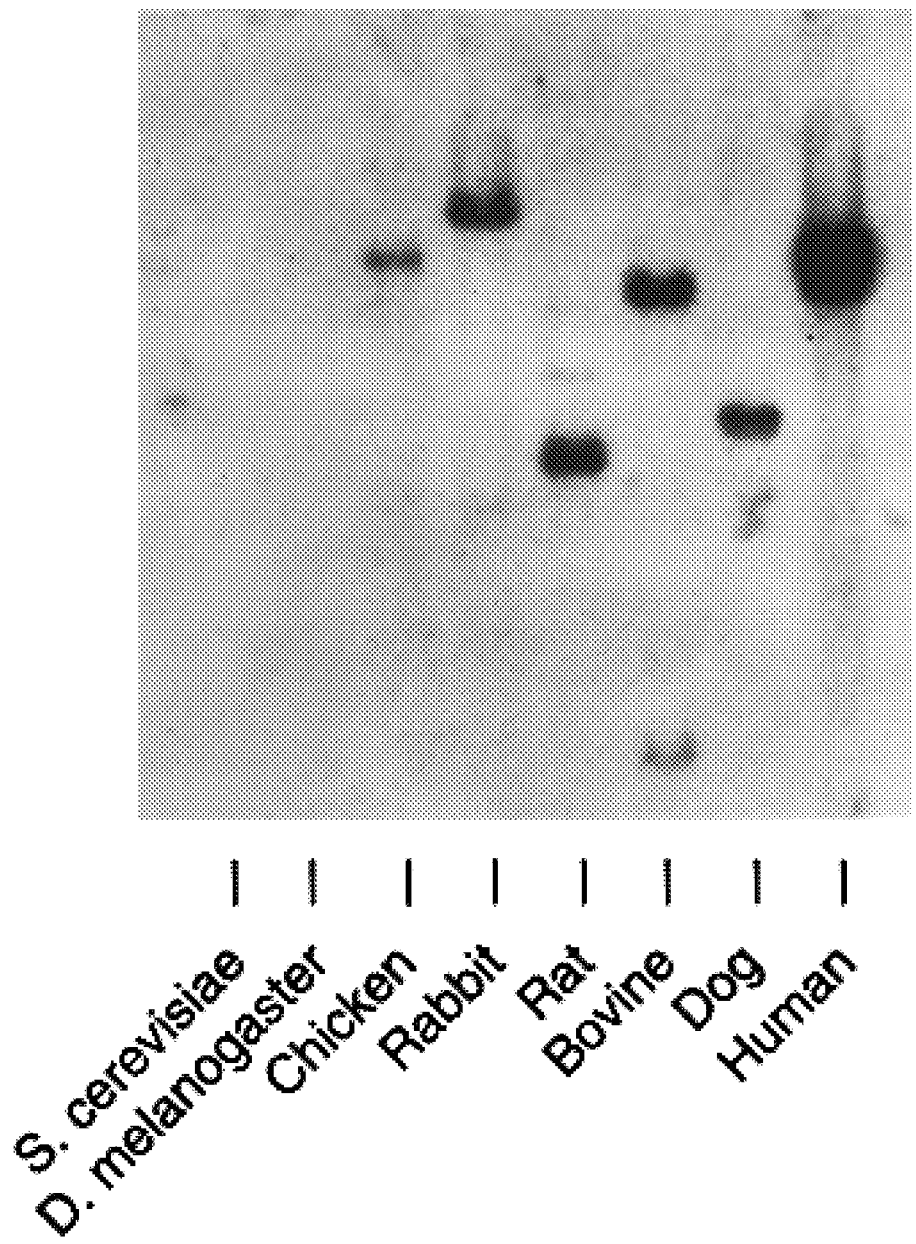

FIG. 4. Southern Analysis of Genomic DNA from various species.

Genomic DNA (10 µg) from several species was digested with Hind III and separated on 1% agarose gels. The filter was probed with rat p55CDC cDNA under medium stringency conditions as defined in Materials and Methods.

FIG. 5. Overexpression of p55CDC cDNA in the sense or antisense orientation in CHO cells results in alteration of growth profiles.

(A) CHOd− cells were transfected with (Δ) PMT, (O) PMTp55s or ((□)) PMTp55as DNA and amplified as described in Materials and Methods. Cells were plated at a starting density of $0.5 \times 10^6$ cells/60 mm dish and counted at the times shown. Arrows indicate the days when media was changed. Each point represents the mean of duplicate counts from parallel cultures which usually varied from 2–14% from the plotted mean.

(B) Flow cytometry analysis of fixed and propidium iodide stained PMTp55s (_) and PMTp55as (_) cells was performed as described in Materials and Methods.

FIG. 6. Immune complexes detected by antibodies against p55CDC. (A) Cell lysates from $^{35}$S-labelled cells in log phase (250 µg on lanes 1,2,3,6,7,8,11,12,13, or 500 µg on lanes 4,5,9,10, and 14) were immunoprecipitated with various antibodies. Immune complexes obtained with 10 µl p34$^{cdc2}$ MAb (lanes 1, 6 and 11), p55CDC competed antiserum (8.4 µg/lane 2,4,7,9,12) and affinity purified p55CDC antiserum (1 µg/lane 3,5,8,10,13,14) were analyzed on 10% SDS-PAGE gels. The dried gel was exposed for autoradiography for 21 hours.

(B) Cell lysates from $^{35}$S-labelled cells in stationary phase (250 µg on lanes 1, 2, 3, 6, 7, 8, 11, 12, 13, or 500 µg on lanes 4,5,9,10,14,15) were immunoprecipitated with various antibodies. Immune complexes obtained with 10 µl p34$^{cdc2}$ MAb (lanes 1,6,11), p55CDC competed antiserum (8.4 µg/lane 2,4,7,9,12,14) or affinity purified p55CDC antibody (1 µg/lane 3,5,8,10,13,15) were analyzed on 10% SDS-PAGE gels. Autoradiography was performed for 1 week.

FIG. 7. Histone H1 kinase activity of p55CDC immune complexes and phosphorylation of p55CDC.

(A) Lysates of CHO cell lines transfected with vector (PMT), vector with sense transcript (PMTp55s), and vector with antisense transcript (PMTp55as) were immunoprecipitated with affinity purified p55CDC antibody. Immune complexes were assayed for histone H1 kinase activity as described in Materials and Methods. (B) CHO cells were labelled with [$^{32}$P]-orthophosphate as detailed in Materials and Methods. Immune complexes obtained from 900 µg lysate precipitated with 1 µg of affinity purified p55CDC antibody (lane 1) or 28 µg of p55CDC competed antiserum (lane 2) were analyzed by SDS-PAGE.

FIG. 8. Immune complexes detected by p55CDC antibodies in Rat 1 and HeLa cells and their kinase activity against a variety of substrates at different stages of the cell cycle.

(A) Lysates (250 µg) from exponentially growing Rat 1 and HeLa cells were immunoprecipitated with p55CDC competed antiserum (lanes 1 and 3), affinity purified p55CDC antibody (lanes 2 and 4), and two different monoclonal antibodies against retinoblastoma protein (lanes 5 and 6).

(B) Lysates (200 µg) from HeLa cells prepared as described in Materials and Methods were immunoprecipitated with either control p55CDC competed antiserum shown in the first lane of each substrate or with affinity purified p55CDC antibody. Kinase assays were performed as described in Materials and Methods with decreasing exogenous substrate concentrations shown from left to right. The histone H1 concentrations in these assays was 0.4 mg/ml, 0.2 mg/ml and 0.1 mg/ml. Myelin basic protein (MBP) and α-casein concentrations decreased from 0.4 mg/ml to 0.1 mg/ml. The control assay was always performed using the highest substrate concentration.

(C) Lysates (200 µg) prepared from HeLa cells as described in Materials and Methods were immunoprecipitated with increasing amounts of affinity purified p55CDC antibody (0.07 µg, 0.28 µg and 1.12 µg). The negative control was done using 4.2 µg of the p55CDC competed antiserum. Kinase assays were performed as described in Materials and Methods using 0.4 mg/ml MBP as the substrate.

(D) Lysates (200 µg) were prepared from HeLa cells at various stages of the cell cycle as described in Materials and Methods and immunoprecipitated with either 8.4 µg p55CDC competed antiserum (lanes 1,8 and 9) or 1.0 µg of affinity purified p55CDC antibody (lanes 2–7). Kinase assays were performed using 0.4 mg/ml H1, 0.4 mg/ml MBP or 0.4 mg/ml α-casein as exogenous substrates.

(E) The excised bands from the dried gel obtained in FIG. 7D were counted. The control values (FIG. 8D lanes 1, 8 and 9) were subtracted from the experimental values (FIG. 8D lanes 2–7) and the results graphed.

FIG. 9. Cycling cells actively translate p55CDC and show high levels of associated α-casein kinase activity when compared to quiescent cells.

(A) Growing and quiescent Rat1 cells were labelled for one hour with $^{35}$S-TRANSLABEL as described in Materials and Methods. Lysates (100 µg) were immunoprecipitated with various antibodies. Immune complexes obtained with 10 µl of p34$^{cdc2}$ MAb (lanes 1 and 7, p55CDC competed antiserum (8.4 µg/ lanes 2 and 8) and affinity purified p55CDC antibody (0.035 µg/ lane 3, 0.14 µg/lanes 4 and 9, 0.56 µg/ lanes 5 and 10, 1.12 µg/lanes 6 and 11) were analyzed by SDS-PAGE.

(B) Lysates (100 µg) were prepared from growing and quiescent Rat1 cells as described in Materials and Methods. Immune complexes were obtained with 10 µl p34$^{cdc2}$ MAb, 8.4 µg of p55CDC competed antiserum and 1.12 µg of affinity purified p55CDC antibody. Kinase assays were performed as described in Materials and Methods using 0.4 mg/ml α-casein as substrate.

DETAILED DESCRIPTION OF THE INVENTION

The present invention relates to a polypeptide designated p55CDC which is involved in mammalian cell division. mRNA transcripts encoding p55CDC were expressed in embryonic tissues and adult hematopoietic tissues which comprise populations of proliferating cells, but were not detected in adult tissues lacking actively dividing cells. Moreover, human hematopoietic cell lines which were induced to differentiate with chemical agents also demonstrated loss of p55CDC transcript as cell division ceased. It has been observed that polypeptides encoded by the rat p55CDC DNA sequence (FIG. 2 and SEQ ID NO:1) and human p55CDC DNA sequence (FIG. 2 and SEQ ID NO:3) have extensive amino acid sequence homology to portions of the cdc4 and cdc20 proteins from Sacchromyces cerevisiae (FIG. 3). As cdc4 and cdc20 are both known to be involved in mitosis and cell division, this homology has suggested involvement of p55CDC in these processes as well. Additional evidence implicating P55CDC in cell division is presented in Example 2. It was shown that down-regulation of p55CDC expression by transfecting host cells with a rat p55CDC anti-sense clone resulted in surviving cells which overproduced sense transcripts, apparently to compensate for the loss of p55CDC mRNA In addition, rat p55CDC appears to be synthesized at high levels in actively growing cells, but not in quiescent cells (Example 5).

p55CDC appears to modulate mitosis and cell division through the formation of a complex with at least one other host cell protein. Complexes containing p55CDC were precipitated by p55CDC antisera from Rat1 cells, HeLa cells, and CHO cells transfected with a rat p55CDC clone. A presumed host cell protein was observed to be associated with p55CDC in each of these cell lines (Examples 3 and 4). The p55CDC complexes from these cell lines displayed kinase activity which fluctuated during the cell cycle. The kinase activity of the p55CDC complex can be distinguished from the activities of other known cell cycle-associated kinases, including cyclin A/CDK2, cyclin E/CDK2 and cyclin B/p34cdc2 complexes, in the following ways: (1) p55CDC complexes had kinase activity against a number of substrates, including histone H1, myelin basic protein and α-casein rather than against a single substrate; and (2) a decrease in p55CDC-associated kinase activity was observed at the G$_1$/S transition and at the G$_2$/M transition. This profile of cell cycle kinase activity has not been previously observed.

The invention provides for an isolated DNA encoding a biologically active p55CDC polypeptide wherein the DNA is selected from the group consisting of:

a) DNA having a nucleotide sequence encoding the amino acid sequence of SEQ ID NO: 2;

b) DNA having a nucleotide sequence encoding the amino acid sequence of SEQ ID NO: 4; and c) DNA having a nucleotide sequence which hybridizes with the DNA of (a) or (b), or with a fragment thereof, wherein the hybridizing DNA encodes a polypeptide having the biological activity of p55CDC.

DNA of the present invention will preferentially hybridize to DNA sequences encoding p55CDC under appropriate conditions of temperature and salt. Establishment of appropriate hybridization conditions is well within the ability of one skilled in the art using published protocols (see e.g., 63). As an example, hybridizations may be performed at 42° in 40% formamide and 5×SSPE for at least 12 hours, followed by three washes in 2×SSC, 0.1% SDS at 50° and one wash in 0.5×SSC, 0.1% SDS for 30 minutes. Sequences which hybridize with p55CDC DNA will be related by deletion, insertion, point mutation, frameshift, alternative open reading frame, or mRNA splice variant. Hybridizing sequences may also be antisense nucleic acids (DNA or RNA) which bind to p55CDC DNA or RNA so as to modulate the expression of p55CDC. Antisense nucleic acids may target the p55CDC coding region or regulatory sequences involved in transcription and/or translation of p55CDC.

DNA sequences hybridizing to p55CDC DNA will preferably encode for a polypeptide having the biological activity of p55CDC. As shown in Examples 3 and 4, p55CDC associates with one or more host proteins to form a complex wherein said complex has cell cycle-dependent kinase activity. The biological activity of p55CDC, as described herein, refers to a complex-associated kinase activity which is active on various substrates such as histone H1, α-casein and myelin basic protein, and wherein the kinase activity on one or more substrates is modulated during the cell cycle. For example, the kinase activity of p55CDC complexes on α-casein is diminished during the $G_1/S$ and $G_2/M$ transitions of the mammalian cell cycle.

The invention also relates to a p55CDC polypeptide as the product of procaryotic or eucaryotic expression of an exogenous DNA sequence, that is, p55CDC is preferably recombinant p55CDC. Exogenous DNA encoding p55CDC may be genomic DNA, cDNA, or may be partially or completely synthetic DNA. In one embodiment, p55CDC DNA includes one or more codons which are preferred for expression in procaryotic host cells, especially *E. coli* host cells. Synthesis of DNA fragments for assembly into sequences for p55CDC expression is accomplished using synthetic methods which are readily available to one skilled in the art, such as those described in Engels et al. (Angew. Chem. Intl. Ed. 28, 716–734 (1989)).

Also provided by the invention are plasmids and host cells for the expression of p55CDC protein. p55CDC expression may be accomplished in procaryotic or eucaryotic hosts (e.g., mammalian, plant or insect cells, yeast or bacterial cells). Preferred host cells include mammalian cells, such as Chinese Hamster Ovary (CHO) cells, or bacterial hosts such as *Escherichia coli*. p55CDC may be expressed from a variety of plasmid or viral vectors which are appropriate for the host cell being used. The use of vector pMT for the expression of rat p55CDC in CHO cells is described in Example 2. However, other vectors that are suitable for p55CDC expression in other host cells may also be used. Expression of p55CDC in transgenic animals may be obtained using expression vectors and DNA transfection procedures available to one skilled in the art.

A method for producing a p55CDC polypeptide is also included. The method comprises culturing a procaryotic or eucaryotic host cell into which an expression vector containing a p55CDC DNA sequence has been transformed or transfected such that a p55CDC polypeptide is expressed.

An isolated p55CDC polypeptide is encompassed by the present invention. Such polypeptides may be produced by expression of DNA molecules encoding p55CDC, or they may be produced by chemical synthesis of peptides using procedures available to one skilled in the art. p55CDC polypeptides produced by the aforementioned biological or chemical methods are isolated using purification techniques which are known to one skilled in the art. p55CDC polypeptides may be analogs of rat or human polypeptides shown in SEQ ID NO: 2 or SEQ ID NO: 4, respectively, wherein said analogs comprise the substitution, deletion or insertion of one or more amino acids. In addition, chemical synthesis of p55CDC polypeptides allows the inclusion of non-naturally occurring amino acids (e.g., D-amino acids) at selected positions. Amino acid residues within the p55CDC polypeptide which are required for activity are determined by generating analogs and testing said analogs for activity, such as the ability to form a complex having cell cycle associated kinase activity, or the ability to advance a host cell through the cell cycle. Protein kinase assays described in Materials and Methods can be used to test for the biological activity of p55CDC analogs. Selected regions of a p55CDC polypeptide, such as those which show homology to the cell division proteins cdc4 and cdc20 (see FIG. 3), may be used to design biologically active p55CDC analogs or peptide fragments. These regions are referred to as GE repeats and are likely to be important in the structure and/or function of p55CDC.

Antibodies specifically binding p55CDC polypeptides of the invention are also provided. Antibodies may be polyclonal or monoclonal and may recognize fragments, analogs and fusion polypeptides of p55CDC as well as the intact protein. Mouse anti-p55CDC antibodies may be produced by techniques available to one skilled in the art and may be modified to form chimeric or humanized antibodies. Anti-p55CDC antibodies are useful in assays described below for quantitating p55CDC and p55CDC complexes that are present in biological samples.

A complex comprising p55CDC and at least one other host cell protein is also provided. Example 3 describes an immune complex from tranfected CHO cells having p55CDC and an associated 210 kDa protein wherein the complex has cell cycle associated kinase activity. Example 4 describes immune complexes from rat 1 and Hela cells which have p55CDC associated with a second polypeptide and exhibit kinase activity. A 110 kDa protein was identified in rat immune complexes and a 100 kDa protein was identified in Hela immune complexes. The ability of p55CDC to associate with at least one other polypeptide such that the resulting complex phosphorylates various host cell molecules appears to correlate with the ability of p55CDC to modulate the cell cycle. Also encompassed by the invention are complexes comprising a p55CDC analog and at least one other host cell protein. In a preferred embodiment, p55CDC complexes will have cell cycle dependent kinase activity such as that described in Example 4.

The invention also relates to a method for detecting levels of p55CDC in biological samples. The method comprises incubating an antibody specifically binding p55CDC, or a fragment, analog, or fusion polypeptide thereof, with a sample under conditions suitable for forming a complex between the antibody and p55CDC and detecting the presence of a p55CDC-antibody complex. The antibody may also bind to p55CDC when p55CDC is complexed with other host cell proteins. Therefore, the method also encompasses the detection of p55CDC complexes. Since p55CDC is present in actively dividing cells, but not in quiescent cells, it is anticipated that a diagnostic assay for p55CDC will be most useful in identifying those samples having elevated levels of cell division.

Methods for modulating cell division are also provided. It will be appreciated by one skilled in the art that compounds which modulate p55CDC activity will modulate cell cycle activity as well. Compounds which modulate the synthesis of p55CDC and/or modulate the ability of p55CDC to form a complex having cell cycle associated kinase activity may be identified using the procedures described for determining p55CDC activity. Modulation of p55CDC kinase activity may involve an increase or decrease in activity at certain periods during the cell cycle which may lead to alterations in the timing or specificity of p55CDC complex activity, Compounds which in turn may be used to control cell division include, but are not limited to, the following: (1) compounds which increase or decrease the levels of p55CDC synthesis; (2) compounds which bind to p55CDC so as to interfere with formation of a p55CDC complex having kinase activity; (3) compounds which compete with p55CDC for complex formation and themselves form inactive complexes; and (4) compounds which promote the formation of the p55CDC complex or stabilize said complex from dissociation by increasing the half-life. Examples include nucleic acid molecules which bind to p55CDC DNA or p55CDC polypeptides, antibodies, peptides, organic molecules, and carbohydrates. Such compounds are identified by screening large repetoires, or libraries, comprising nucleic acids, peptides or small organic molecules derived from chemical synthesis or natural sources (e.g., bacteria, fungi, plants). Considerable literature exists on the synthesis, characterization and screening of very large natural or synthetic libraries of molecules or polymers. One skilled in the art would appreciate that such libraries can be screened for compounds that modulate p55CDC activity.

Compounds which inhibit the biosynthesis or activity of p55CDC are useful in inhibiting the growth of those tumor cells having increased levels of p55CDC or increased levels of cell cycle dependent kinase activity associated with p55CDC as compared to normal, noncancerous cells. Compounds useful as chemotherapeutic agents include, but are not limited to, the following: (1) compounds which decrease the levels of p55CDC synthesis; (2) compounds which bind to p55CDC so as to interfere with formation of a p55CDC-host cell protein complex having kinase activity; and (3) compounds which compete with p55CDC for association with one or more host cell proteins involved in complex formation and themselves form inactive complexes. Tumor cells which grow more rapidly than normal, noncancerous cells perhaps by virtue of increased p55CDC activity may be more responsive to p55CDC-inhibiting agents. Such agents would be expected to have less effect on p55CDC activity in normal cells.

A method of chemotherapy comprising treating a mammal with an amount of a compound which is effective in reducing or inhibiting p55CDC activity in a pharmaceutically effective adjuvant is also provided. Compounds which reduce or inhibit p55CDC activity are identified by screening appropriate sources for activity against p55CDC using assays for p55CDC activity as described herein. A dosage which is effective in reducing or inhibiting p55CDC activity may be determined by one skilled in the art taking into account such factors as the condition being treated and administration regimen. Important considerations include the type and location of the tumor being treated and whether the route of administration is by injection (intravenous, intramuscular, or subcutaneous) or by oral or nasal intake. Compounds of the present invention are mixed with a pharmaceutically acceptable adjuvant which may include any suitable buffer, solubilizer, preservative, carrier or antioxidant. Preferably, the adjuvant will not decrease the p55CDC-inhibiting activity of the compound. An extensive survey of pharmaceutically acceptable ajuvants is found in Remington's *Pharmaceutical Sciences,* 18th ed. A. R. Gennaro, ed. Mack, Easton, Pa. (1990).

EXAMPLE 1

IDENTIFICATION AND CHARACTERIZATION OF p55CDC

The D55CDC gene

The gene encoding p55CDC was identified serendipitously during an attempt to identify novel glycosyltransferase enzymes by low stringency screening of a rat genomic library with cDNA encoding the rat α2,6 sialyltransferase (57,73). During one round of screening, a genomic clone was isolated. Restriction map analysis first narrowed the hybridizing region to a 2 kb Bgl II fragment. The cross hybridizing region of this fragment was further narrowed to a 0.26 kb Pst I fragment which was used for Northern analysis of various embryonic, neonatal and adult rat tissues.. This identified a tissue which could be used as a source of RNA for construction of a cDNA library.

Northern analysis revealed tissue-specific and developmentally-regulated expression of a unique transcript (FIG. 1A). A 2 kb mRNA was abundant in RNA from total rat embryo, and this transcript was enriched in embryonic rat liver. However, in two day old neonatal rats, the level of message in the liver decreased precipitously. The transcript was still abundant in spleen from 2 day old rats, and a small amount was present in kidney. In 16 day old rats, the transcript was still abundant in spleen and thymus, but was barely detectable in liver and kidney. The transcript was not detectable in any adult tissues, although a longer exposure of a blot containing more RNA did reveal a faint band in the spleen sample. The presence of the transcript in hematopoietic tissues, such as neonatal liver, thymus and spleen, suggested that expression of this novel gene was highest in tissues in which cell proliferation was occuring.

A cDNA library was constructed using polyA+ RNA from two day old rat spleen. Using the Pst I genomic fragment as a probe, several positive plaques were identified, at a frequency of approximately 1:15,000. The two largest cDNA inserts were subcloned and sequenced. The nucleotide sequence (FIG. 2 and SEQ ID NO: 1) coded for a protein of 499 amino acids, with a predicted molecular mass of 55 kDa. However, this sequence did not appear to encode a classical glycosyltransferase enzyme, since there was no evidence of an amino-terminal hydrophobic membrane spanning signal-anchor domain, which is essential for glycosyltransferases to be properly oriented in the Golgi (57).

The human p55CDC gene was isolated from an HT1080 cell line cDNA library by the following procedures. The nucleotide sequence and deduced amino acid sequence are shown in FIG. 2 and in SEQ ID NO: 3. A comparison of the open reading frames of the rat and human sequences showed an 87% identity at the nucleotide level, which increased to 95% at the amino acid level. Differences in the human nucleotide sequence are shown above the rat sequence, and differences in the human amino acid sequence are shown below. The human sequence diverged considerably from the rat upstream of the ATG start site, and also in the 3' untranslated region.

Homology of p55CDC to cell cycle proteins

A search of the genEMBL database revealed that rat and human p55CDC proteins had seven regions of homology with the WD-40 repeat of the β subunit of G proteins (27) (FIG. 3A), and to a number of proteins which contain this imperfect repeat motif (for review, see 12,72). These included the products of the *S. cerevisiae* genes CDC20 (65) and CDC4 (77), TUP1/AER2 (78), PRP4 (58), and MSI1 (62), as well as the products of the *D. melanogaster* gene Espl, the *D. discoidum* gene AAC3 (66), the *Arabidopsis thaliana* gene COP1 (13) and the dTAF$_{11}$80 subunit of Drosophila TF11D (22). The highest degree of homology, illustrated in FIG. 3B, was seen between p55CDC and the two *S. cerevisiae* cell division cycle proteins, Cdc20 (519 amino acids) and Cdc4 (779 amino acids). The BESTFIT analysis revealed a 45% identity between amino acids 172–407 of p55CDC and amino acids 249–479 of the Cdc20 protein, which increased to 59% when highly conserved substitutions were included. This was the only protein in which a high degree of similarity was found with the degenerate internal Gβ-repeats in p55CDC. The Cdc4 protein was the only protein which showed strong homology with all seven repeats found in p55CDC, using the first seven of the nine repeats found in the Cdc4 protein (FIG. 3B). The alignment of the highly degenerate WD-40 repeats in these two proteins required the introduction of 16 gaps over 300 amino acid residues. This comparison indicated that 28% of the residues in this region were identical, and 41% were identical or highly conserved. Notably, the *S.*

*cerevisiae* Cdc20 and Cdc4 proteins each displayed a greater degree of homology to the mammalian p55CDC protein than they did to each other.

Recently a clone isolated from a Xenopus oocyte cDNA library by virtue of its ability to suppress the temperature sensitive defect of the *S. Cerevisiae* cdc15 mutation, was shown to encode a protein of 518 amino acids that has seven Gβ-repeats in its carboxy terminal half (69). This protein called βTrCP (β-transducin repeat containing protein) was not a functional homolog of CDC20, though overexpression of both these genes is capable of suppressing the cdc15 mutation (1,69). Both βTrCP and p55CDC have seven Gβ-repeats and show 24% identity over this region.

The only protein that showed significant homology to p55CDC extending beyond the Gβ- repeats was the *S. cerevisiae* MSI1 protein, which is a negative regulator of the RAS-mediated induction of cAMP levels (62). The MSI1 protein (422 amino acids) was 24% identical to p55CDC, and this increased to 28% when only the amino terminal 178 residues of p55CDC were compared to the amino terminal 148 residues of MSI1.

Cross species homology of p55CDC

A high degree of evolutionary conservation within the p55CDC open reading frame was seen when genomic DNA from a variety of mammalian species, chicken, *D. melanogaster* and *S. cerevisiae* were examined by Southern blot analysis, using the rat cDNA probe (FIG. 4). A cross-hybridizing species was detectable in all the mammalian and the avian species, although no bands were seen in the lanes containing *S. cerevisiae* and *D. melanogaster* DNA. These results also indicate that the gene encoding p55CDC is a single copy gene, with no closely related genes in the species examined.

Expression of p55CDC in tissues and cell lines

The pattern of expression of p55CDC mRNA in embryonic and neonatal rat tissues, and the apparent relationship between p55CDC and the *S. cerevisiae* Cdc20 and Cdc4 proteins suggesting a possible role for p55CDC in cell division, prompted us to examine other developing mammalian tissues for p55CDC expression. Northern analysis of human tissues demonstrated a pattern of expression similar to that seen in the rat, with high levels of expression in fetal liver and juvenile thymus, but no expression seen in fetal lung, adult lung or liver, or adult buffy coat, which is primarily comprised of non-dividing white blood cells (FIG. 1B). A second Northern analysis examining polyA+ RNA from adult human heart, brain, placenta, lung, liver, skeletal muscle, kidney and pancreas demonstrated expression of p55CDC in only one tissue, the placenta, which contains actively dividing cells; a similar pattern of expression has been described for p34$^{cdc2}$ (48).

Figure 1C:
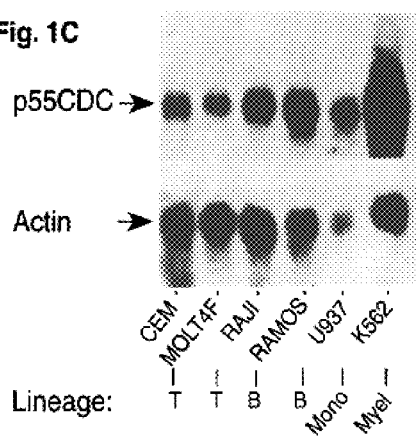

A number of human cell lines also expressed the p55CDC transcript. The transcript was abundant in all leukemia cell lines examined, including the T cell lines MOLT 4f and CEM, the B cell lines Raji and Ramos, the monocytic cell line U937 and the myeloerythroid cell line K562 (FIG. 1C). Indeed, we observed expression of the p55CDC transcript in every cell line examined at log phase of growth, regardless of lineage.

To examine whether expression of the p55CDC transcript was related to the ability of cells to divide, we took advantage of the unique properties of two leukemia cell lines, K-562 and HL-60. K-562 cells can be induced by treatment with sodium butyrate to undergo erythroid differentiation with no significant effect on growth rate (2). In contrast, treatment of K-562 cells with the phorbol ester TPA causes monocytic differentiation accompanied by growth arrest (5).

Figure 1D:
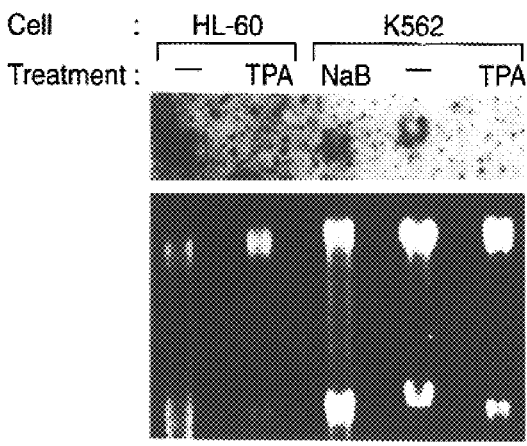

Treatment of HL-60 cells with TPA also causes monocytic differentiation, with arrest of DNA synthesis and cell division (61). We examined the effects of these agents on the level of expression of p55CDC mRNA in these two cell lines (FIG. 1D). The p55 transcript was easily detectable in both mock-treated cell lines. For both K-562 and HL-60, treatment of the cells with TPA resulted in loss of p55CDC mRNA expression. In the K-562 cells treated with sodium butyrate, in which differentiation is not accompanied by growth arrest, the level of p55CDC transcript was roughly equal to that found in the mock-treated cells. These results indicate that p55CDC mRNA is synthesized only in dividing cells.

EXAMPLE 2

EFFECTS OF p55CDC ON CELL PROLIFERATION

Figure 5A:
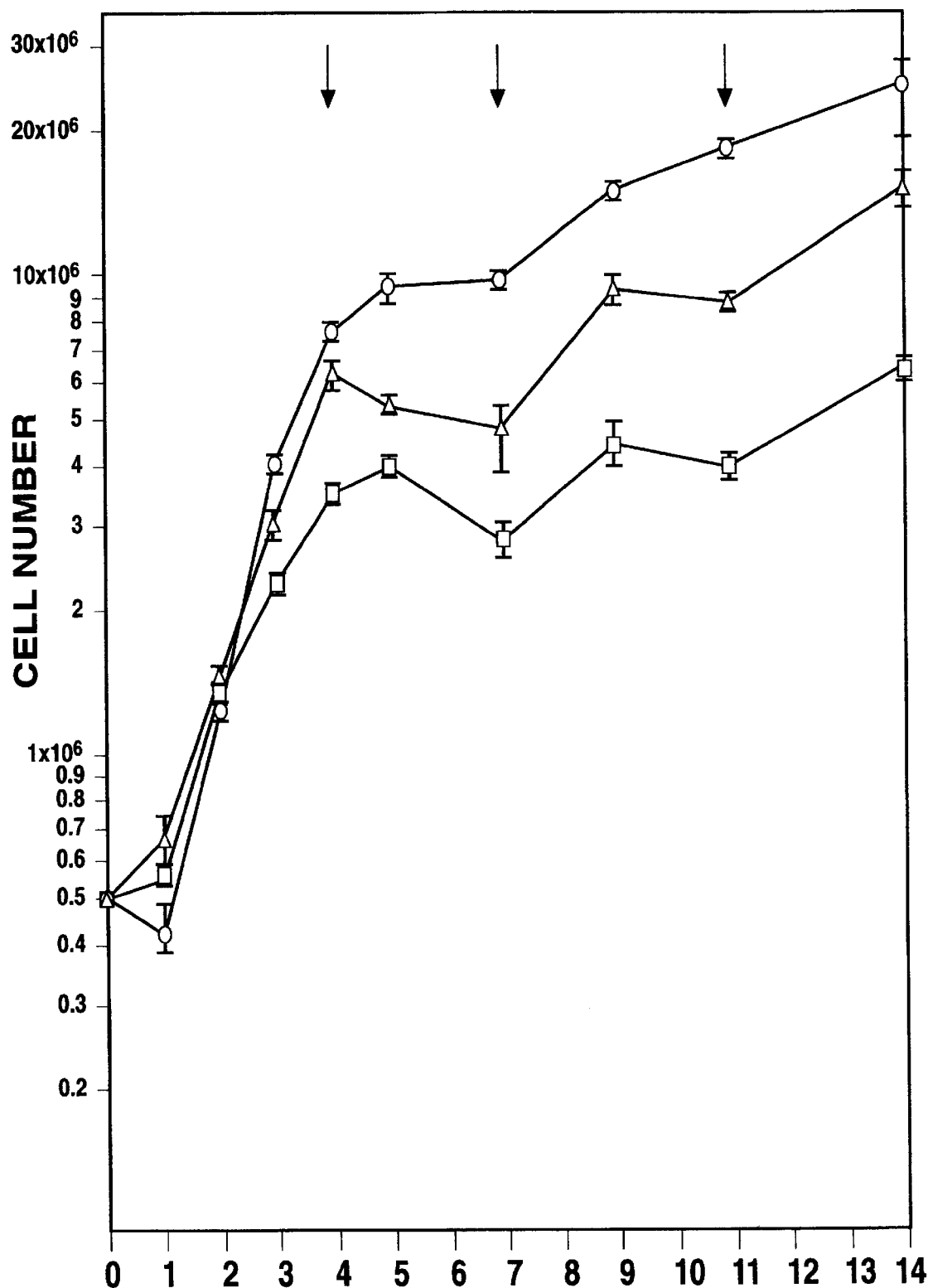
Figure 5B:
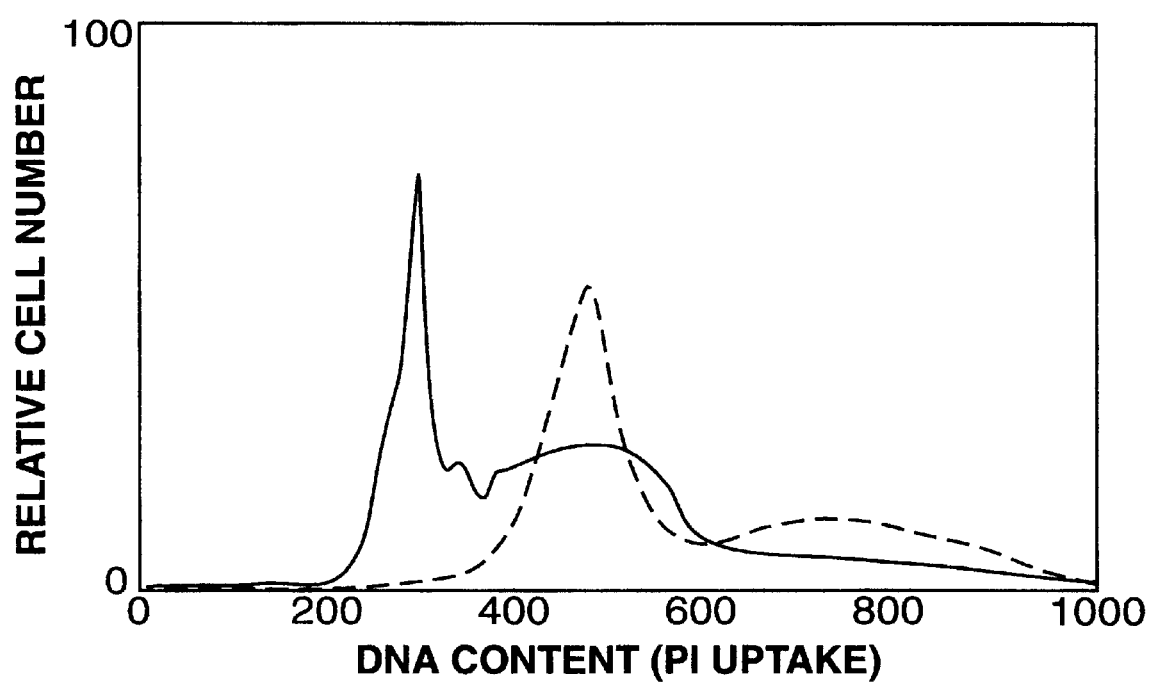

To explore possible functions of the p55CDC protein, CHOd- cells were transfected with plasmid containing the cDNA encoding the rat p55CDC in either the sense (PMTp55s) or antisense (PMTp55as) orientation. A 1.8 kb fragment of rat cDNA was inserted downstream of the metallothionein promoter in the pMT010/A+ mammalian expression vector (9). This vector also contains two dominant selectable markers, the bacterial neo gene and the mouse DHFR gene, driven by the Sv40 promoter. Control cells were transfected with vector alone (PMT). Following amplification with methotrexate, the three pools of cells were plated at a density of 0.5×10$^6$ cells per 60 mm plate in the presence of 0.05 mM zinc, and the growth profiles plotted for fourteen days (FIG. 5A). Pools of transfected cells were studied, rather than individual clones, to minimize the effect of any clonal variation in the CHOd- cells. Initially, little difference in the growth rates were observed among the three pools of transfected cells, although the PMTp55as cells were significantly larger than the PMTp55s or control cells as shown by forward scatter analysis determined by flow cytometry and visual observation under the microscope. Moreover, a DNA content analysis as measured by propidium iodide uptake showed that PMTp55as cells had an increased amount of DNA/cell, indicating that these cells were hyperdiploid (FIG. 5B). As the plates began to reach confluence, dramatic differences in the growth profiles were observed. The PMTp55 as cells reached confluence first, at a lower cell number, consistent with their layer size. After reaching confluence the PMTp55as cells continued to divide slowly. The smaller PMTp55s cells continued to divide at a faster rate after reaching confluence. The PMTp55s cells reached a density of 24×10$^6$ cells/plate by day 14, compared to 6×10$^6$ cells/plate for the PMTp55as cells. The growth profile of the PMT cells fell midway between those of the PMTp55s and PMTp55as cells.

Since the cells transfected with the vector encoding an antisense transcript continued to survive, although with an altered phenotype, we examined the pools of transfected cells for the presence of sense and antisense p55CDC mRNA transcripts using an RNAse protection assay (70). As shown in Table 1, the PMT cells had an average of 166 copies of sense mRNA per cell, while, as expected, the PMTp55s cells had an increased average of 734 copies of sense mRNA per cell. Surprisingly, the PMTp55as cells also had an increased number of copies of sense mRNA, with an average of 714 copies per cell. In addition, the PMTp55as cells had only a moderate amount of antisense mRNA, with an average of 205 copies per cell, despite having been transfected with cDNA encoding the antisense transcript.

This same pattern was observed when clonal cell lines isolated from the pools of cells were analyzed. Each of the four PMTp55as clonal lines made elevated amounts of the sense transcript; in all lines, this amount was at least five times the amount of the antisense transcript. As expected, in the control PMT cells, the average number of copies of sense transcript per cell declined considerably in confluent cells.

TABLE 1 p55CDC mRNA copy number in both sense and antisense orientation in various cell lines

| Cell Line | 48 hours mRNA copies/cell[a] | | 7 days mRNA copies/cell[a] | |
|---|---|---|---|---|
| | Sense | Anti-sense | Sense | Anti-sense |
| PMT | 166 ± 6 | — | 4 ± 7 | — |
| PMTp55s | 734 ± 40 | 21 ± 7 | 240 ± 9 | 16 ± 5 |
| PMTp55as | 714 ± 10 | 205 ± 10 | 263 ± 10 | 96 ± 10 |
| PMTp55A$_2$s | 771 ± 12 | 2 | ND[b] | ND |
| PMTp55B$_6$s | 4136 ± 66 | 117 ± 4 | ND | ND |
| PMTp55B$_{12}$as | 706 ± 20 | 126 ± 3 | ND | ND |
| PMTp55G$_6$as | 1176 ± 10 | 213 ± 14 | ND | ND |
| PMTp55H$_5$as | 928 ± 17 | 157 ± 2 | ND | ND |
| PMTp55H$_{11}$as | 1149 ± 21 | 128 ± 7 | ND | ND |

[a]Values were determined as described in experimental procedures.
[b]Not Determined Genomic DNA analysis of all six clonal cell lines demonstrated that the elevated expression of sense transcripts was not due to amplification of the endogenous gene. The two clonal isolates expressing sense orientation transcripts were distinct from one another. In contrast, it is likely that all four of the PMTp55as clones we isolated derived from the expansion of only one transfected cell in the original pool of cells, since restriction map analyses of the four clonal PMTp55as cell lines using two different restriction enzymes and two different probes, to detect either plasmid or p55CDC sequences, demonstrated identical banding patterns. The results indicated that inhibition of p55CDC expression by antisense transcripts was compensated for by overexpression of sense transcripts. This data suggested that p55CDC was essential for maintenance of cell proliferation in culture.

EXAMPLE 3

IMMUNE COMPLEXES CONTAINING p55CDC

Polyclonal rabbit antiserum was raised against a fusion protein consisting of p55CDC and glutathione S-transferase. Both the original antiserum and an affinity purified antibody preparation precipitated a protein of $M_r$ 55 kDa from an in vitro transcription/translation reaction containing p55CDC cDNA, consistent with the predicted mass of the polypeptide.

Figure 6A:
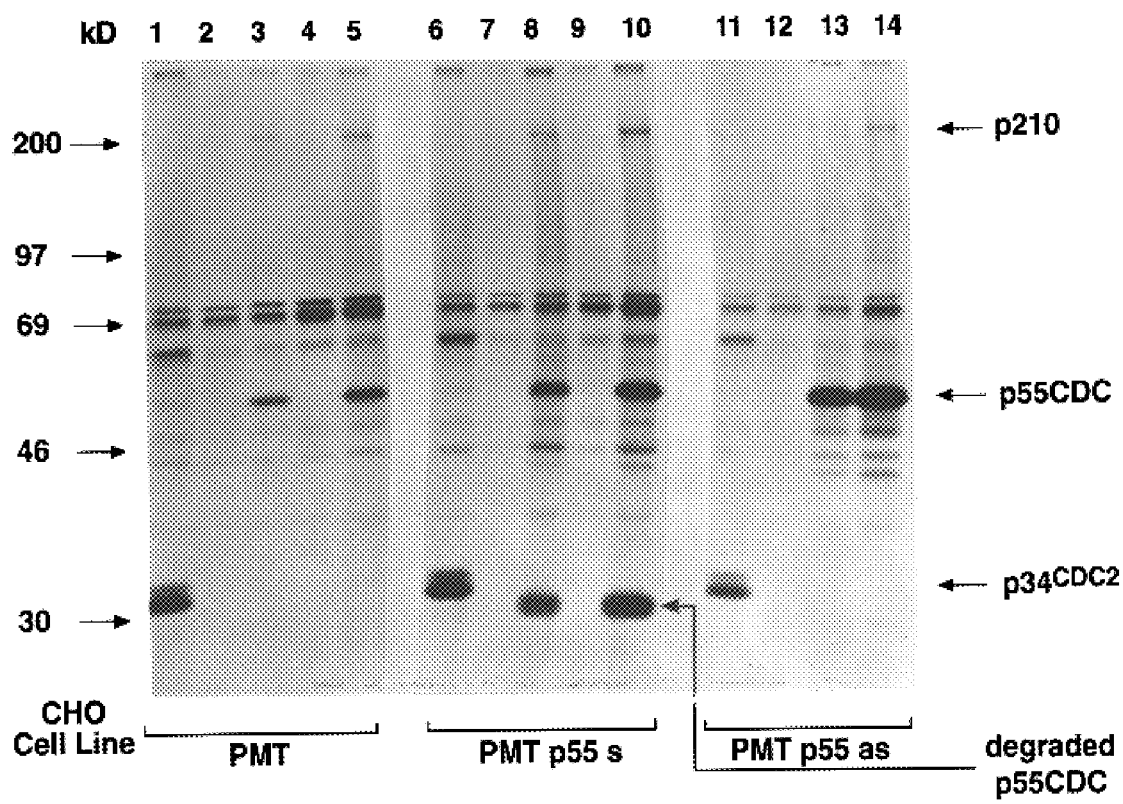
Figure 6B:
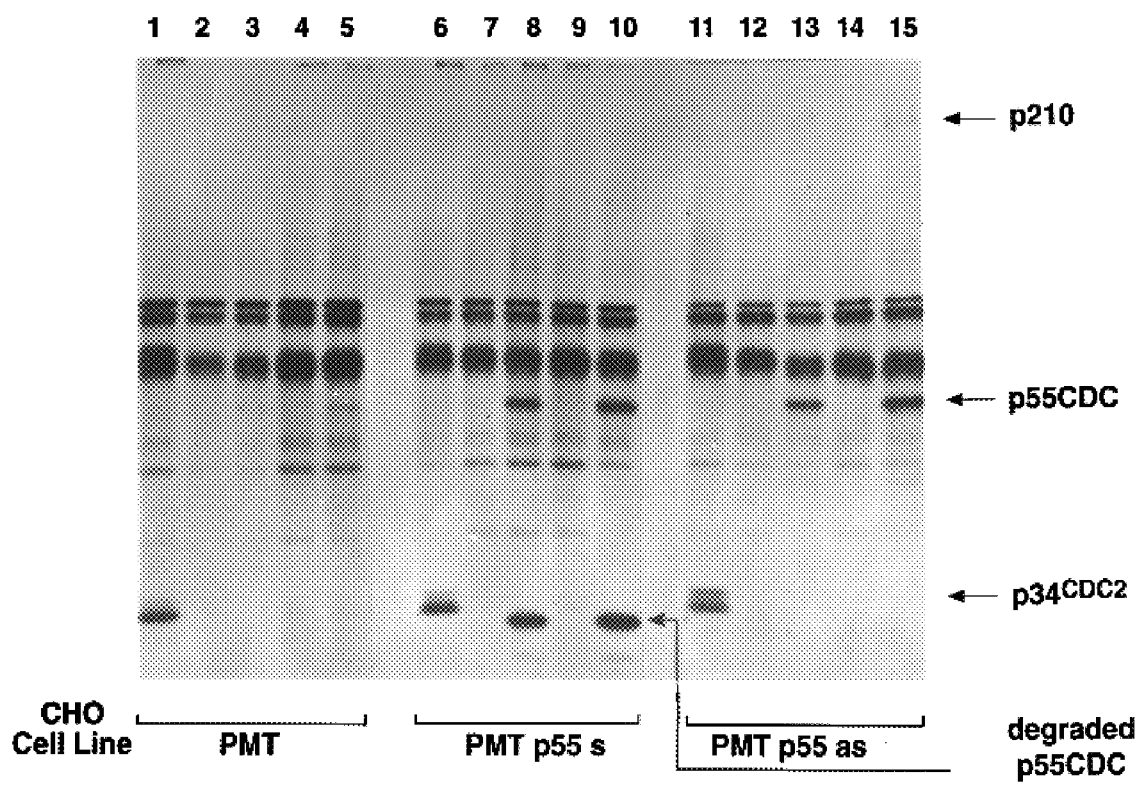

To examine the level of p55CDC production in the transfected cell lines, immunoprecipitations were performed on extracts of $^{35}$S-labelled cells in log phase, using the affinity purified antibody. As shown in FIG. 6A, the PMTp55s and PMTp55as cells had increased levels of p55CDC compared to the PMT cells, consistent with the demonstration of increased numbers of transcripts encoding p55CDC in these cells. In the PMTp55s cells, there was a strong band of 31 kDa which probably represents a degradation product of p55CDC, since this band was also detected on immunoblot analyses of cell extracts using the polyclonal antibody preparation. This 31 kDa band was also observed when cell lysates were prepared without protease inhibitors, and no intact p55CDC was detected in the absence of protease inhibitors. This peptide was not p34$^{cdc2}$, since no p34$^{cdc2}$ protein was detected in any of the immune complexes.

Immunoprecipitates of p55CDC also contained a protein of $M_r$ 210 kDa. The amount of p210 detected in the immunoprecipitates was roughly proportional to the amount of p55CDC. When this experiment was repeated on cells in stationary phase, seven days after plating, a significant decrease in the amounts of both p55CDC and p210 is observed (FIG. 6B); in FIG. 6B, a one week exposure of the autoradiogram was required to detect p55CDC, compared to a 21 hour exposure in FIG. 6A. These results indicate that production of p55CDC is highest in proliferating cells.

EXAMPLE 4

KINASE ACTIVITY OF p55CDC IMMUNE COMPLEXES

Figure 7A:
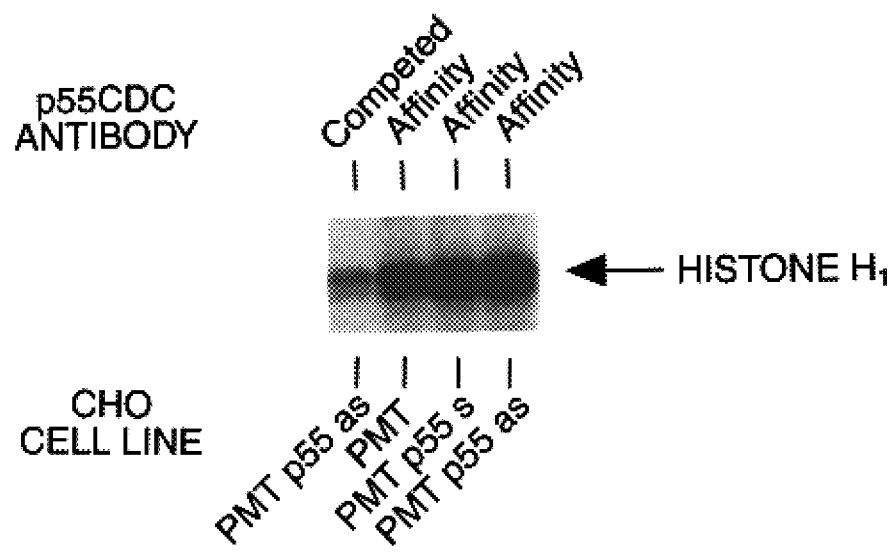
Figure 7B:
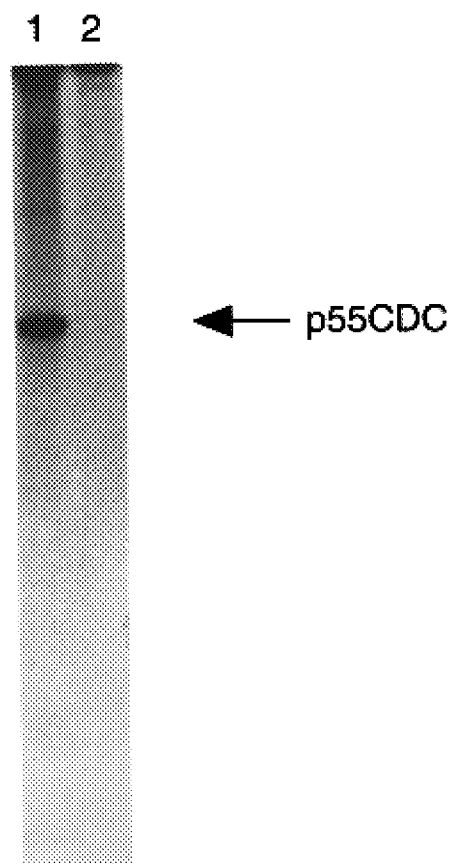

Since many events in the cell cycle are controlled by various kinases, it was of interest to determine whether p55CDC immune complexes had any kinase activity. All immune complexes examined for protein kinase activity were precipitated under conditions identical to those used in FIG. 6. The immunoprecipiptation buffer was formulated (1% NP-40, 1% deoxycholate and 0.1% SDS) to minimize non-specific protein association. A number of cell division kinases can phosphorylate histone H1, so this substrate was assayed first. As shown in FIG. 7A, immune complexes precipitated with p55CDC antibody phosphorylated histone H1. Immune complexes prepared from lysates of the PMT, PMTp55s and PMTp55as cells all demonstrated kinase activity against histone H1. The highest levels of phosphorylation were seen in the PMTp55s and PMTp55as cells which have increased expression of p55CDC. In the negative controls, using competed antiserum, a small amount of residual activity is seen. In reactions performed without addition of exogenous substrates, no phosphorylated proteins were detected, indicating that none of the proteins in the immune complex are endogenous substrates of the kinase activity. However, when all three pools of transfected cells were labelled with [32p]- orthophosphate and p55CDC was immunoprecipitated, SDS-PAGE analysis revealed that p55CDC was phosphorylated (FIG. 7B). Thus, p55CDC is a substrate of another endogenous kinase in the CHO cells. In the PMTp55s cells, no $^{32}$P-labelled 31 kDa band was detected (see FIG. 6A and B, lanes 8 and 10), indicating that the 31 kDa degradation fragment of p55CDC is either not phosphorylated, or is dephosphorylated prior to degradation.

Figure 8A:
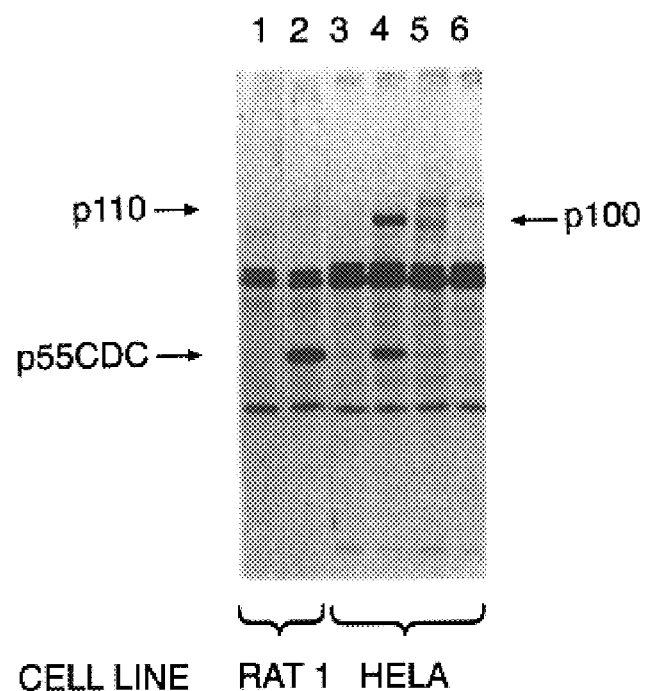

We wished to examine whether p55CDC in different cell lines was associated with other proteins in immune complexes and whether these complexes also had kinase activity. The Rat1 fibroblast and HeLa cell lines were chosen for this analysis. Proliferating Rat1 and HeLa cells were lysed, and immune complexes precipitated with the affinity purified p55CDC antibody (FIG. 8A, lanes 2 and 4). SDS-PAGE analysis of the immune complexes did not reveal the 210 kDa band seen in CHO cells, but did reveal other discrete bands which appeared to be cell-specific. In the Rat1 cells, a protein of 110 kDa was present in the p55CDC immune complexes, while a protein of 100 kDa was seen in p55CDC immune complexes in HeLa cells.

Figure 8B:
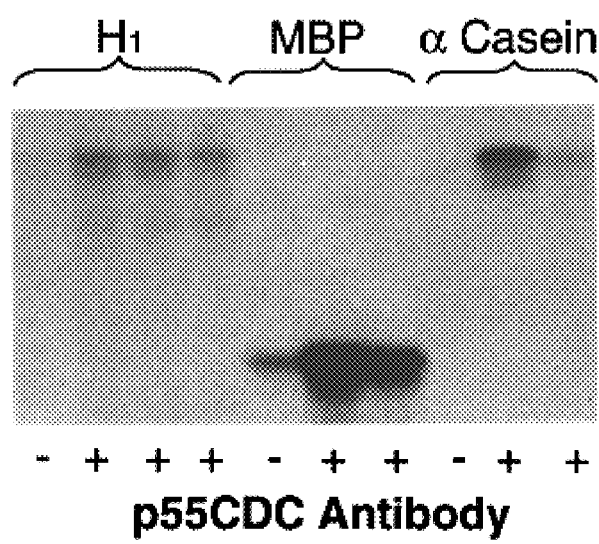
Figure 8C:
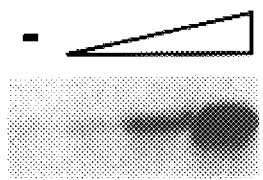

The p55CDC immune complexes from HeLa cells were examined for kinase activity against a number of different substrates (FIG. 8B). Kinase activity was detected with histone H1, myelin basic protein and α-casein, with maximal activity detected with myelin basic protein. β-casein was also examined, but minimal activity was detected with β-casein as a substrate (data not shown). The level of kinase activity correlated with p55CDC concentration, since increasing the amount of antibody used for the immunoprecipitation resulted in increased phosphorylation of myelin basic protein (FIG. 8C).

Figure 8D:
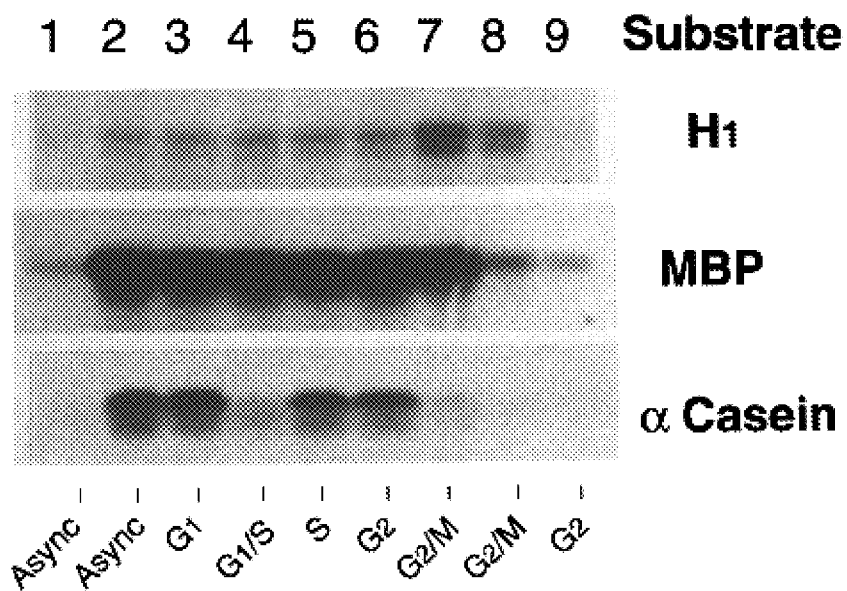
Figure 8E:
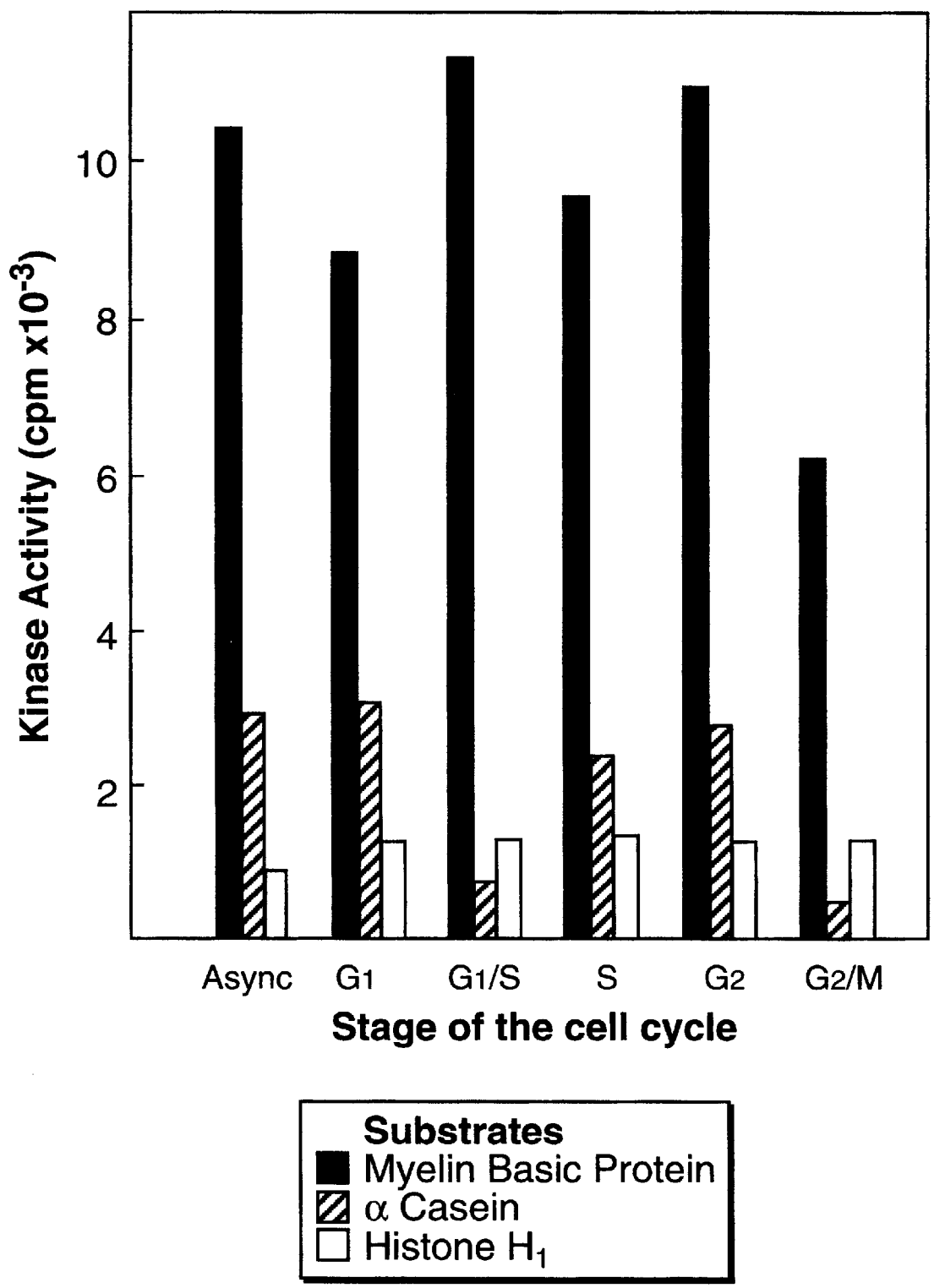

To determine whether the p55CDC-associated kinase activity fluctuated during the cell cycle, as has been described for the cyclin-dependent kinases, cells were arrested at various points in the cell cycle and immune complexes precipitated from cell lysates were examined for kinase activity. A distinct pattern of a cell cycle related fluctuation in kinase activity was detected with only one of the three substrates examined, α-casein (FIGS. 8D and E). Kinase activity against α-casein was present in HeLa cells and in cells blocked in $G_1$ by serum starvation. The level of activity against α-casein dropped approximately four-fold in cells arrested at $G_1/S$ and returned to the higher levels in cells harvested during S phase. Kinase activity remained constant in cells in the $G_2$ stage of the cell cycle and decreased six-fold in cells at the G2/M transition. Kinase activity against histone H1 by p55CDC immune complexes was stable throughout the cell cycle (FIG. 8E). Background levels of histone H1 kinase activity in the $G_2/M$ cells (FIG. 8D, lane 8) was most likely due to residual p34cdc2 kinase activity in these samples. Kinase activity against myelin basic protein was also relatively constant throughout the cell cycle, with the exception of the $G_2/M$ transition, where a two-fold decrease in activity was observed. While p55CDC was difficult to detect by immunoblotting of cell lysates prepared from cells at any of the various stages, the amount of p55CDC present in cells did not appear to fluctuate during the cell cycle, in contrast to the fluctuation in kinase activity observed with p55CDC immune complexes.

EXAMPLE 5 p55CDC EXPRESSION AND KINASE ACTIVITY IN GROWING AND QUIESCENT CELLS

Figure 9A:
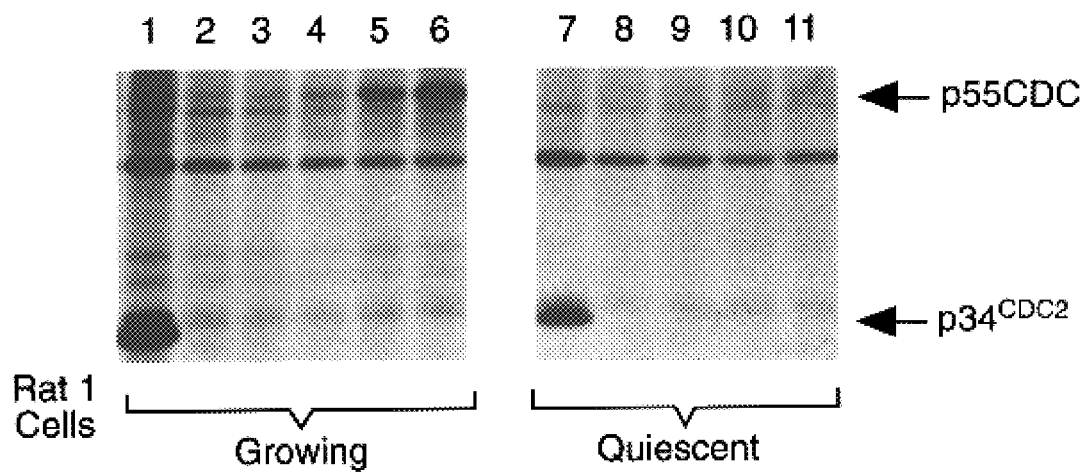
Figure 9B:
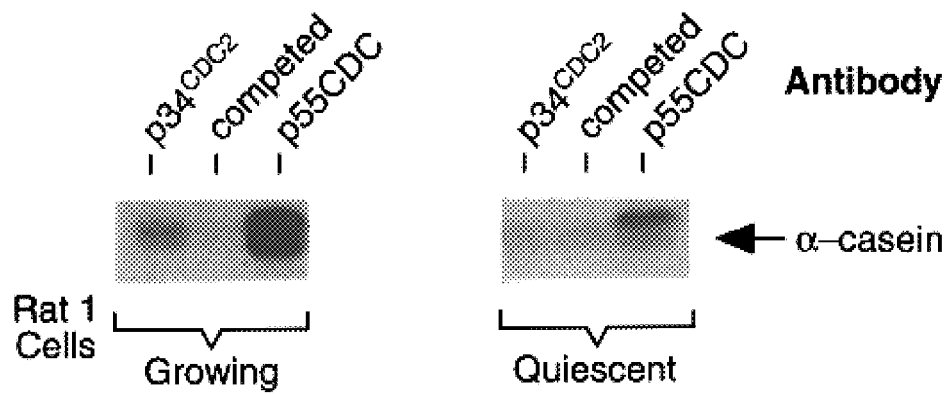

The expression of p55CDC and the associated kinase activity in growing and quiescent populations of cells was compared by exploiting the ability of Rat1 cells to arrest growth under limiting serum conditions. As shown in FIG. 9A, exponentially growing Rat1 cells actively synthesized labelled p55CDC (lanes 3–6), while the quiescent population showed minimal production of p55CDC within the one hour labelling period (lanes 9–11). To rule out that the kinase activity we observed was precipated non-specifically from the cell lysates, increasing amounts of p55CDC antibody were used in the immunoprecipitations. As shown in lanes 3–6, increasing the amount of p55CDC antibody resulted in the precipitation of increasing levels of p55CDC. This result is consistent with the result observed in FIG. 8C, where increasing the amount of antibody used for precipitation increased the level of p55CDC kinase activity detected. The production of labelled $p34^{cdc2}$ is also substantially reduced in the quiescent population (compare lanes 1 and 7), although the amount of total $p34^{cdc2}$ in the two samples was virtually equivalent, as detected on Coomassie blue stained gels of immunoprecipitated material. We also examined the p55CDC associated kinase activity under these two conditions and compared it to that observed for $p34^{cdc2}$ immune complexes as a control. A higher level of activity was observed with the p55CDC complexes using α-casein as a substrate, since α-casein is a poor substrate for the $p34^{cdc2}$ kinase (FIG. 9B). Both the $p34^{cdc2}$ kinase and the p55CDC associated kinase showed a decrease in activity in the quiescent cells. As seen in the HeLa cells, when myelin basic protein was used as a substrate, no significant change in the p55CDC associated kinase activity was observed.

MATERIALS AND METHODS

RNA Analysis

Total RNA was prepared from freshly dissected rat tissues, human thymus and buffy coat, by the method of Chomczynski and Sacchi (8). mRNA from human cell lines was prepared by the FASTRACK kit (Invitrogen). Gel electrophoresis of total RNA (30 μg/lane) was done in 1% agarose gels containing formaldehyde and Northern hybridizations were performed as reported earlier (73). Radiolabelled probes were generated using the Amersham Multiprime DNA labelling system RPN.1601. mRNA size was determined by comparing with commercial RNA standards (Bethesda Research Laboratories, Gaithersburg, Md.). mRNA from other human tissues was purchased from Clontech as was a multiple human tissue Northern blot.

To generate the riboprobes for the RNAse protection assay, the gel purified p55CDC CDNA fragment was subcloned into BLUESCRIPT (Stratagene, LaJolla, Calif.) in both the sense and antisense orientation relative to the T7 promoter. All subsequent steps were performed as described previously (70). Briefly, cells ($1 \times 10^6$/ml) were washed in phosphate buffered saline (PBS) and lysed by incubation at room temperature for 20 minutes in 10 mM Tris pH8.0, 1 mM EDTA, 20 mM dithiothreitol, 100 μg/ml proteinase K and 0.2% SDS. Lysed samples were added to hybridization mix with the labelled riboprobe and incubated at 84° for 2 hours. Following RNAse digestion for 20 minutes at 37° using RNAse A and RNAse T1, the sample was loaded onto a SEPHACRYL S200 Superfine gel filtration column (Sigma, St. Louis, Mo.) and the void volume fraction containing the protected probe was counted. The quantity of gene specific RNA was calculated from a standard curve. All assays were performed in duplicate.

DNA Analysis

Genomic Southerns and restriction map analysis were performed using standard molecular biology techniques (63). Genomic DNA from various species was purchased from Clontech (Palo Alto, Calif.). Medium stringency hybridizations were performed at 42° in 40% formamide. All hybridizations were performed at a salt concentration of 5×SSPE. Following overnight hybridizations the filters were washed three times in 2×SSC, 0.1% SDS at 50°. The final wash was done in 0.5×SSC, 0.1% SDS for 30 minutes. DNA sequence was determined using Sequenase (U.S. Biochemical), following the manufacturer's protocol. SEQUENCING was also performed on the Applied Biosystems 373A automated DNA sequencer using the Tag Dye Deoxy Terminator kit according to suggested protocol. The comparative percent identity values between the genes carrying the Gβ motif were obtained using the GCG BESTFIT program with gap weight set at 2.0 and length weight at 0.05.

cDNA Cloning of Rat D55CDC

A rat genomic library made from a partial EcoRI digest ligated into Charon 4A (Clontech) was screened at low stringency (hybridizations performed in 43% formamide at 37°) with a 435 base pair cDNA probe encompassing amino acid residues 141–286 of the a2,6 sialytransferase gene (73). Restriction map analysis of the isolated genomic clone revealed a 2 kb Bgl II fragment that hybridized to the probe. This fragment was subcloned into a pUC vector and further analysis narrowed the hybridizing region to a 0.26 kb Pst 1 fragment which was used in all subsequent analysis. PolyA+ RNA from newborn rat spleen was selected by two cycles of binding to oligo (dT)-cellulose type 2 (Collaborative Research). A cDNA library was constructed using the Pharmacia cDNA synthesis kit followed by ligation into the 1gt10 vector. This was packaged using the GIGAPACK II Gold cloning kit (Stratagene). An initial packaging reaction gave $3.3 \times 10^6$ pfu and $1 \times 10^6$ pfu were screened using the 0.26 kb Pst I fragment as probe.

cDNA Cloning of Human p55CDC

The human HT1080 cell line cDNA library was constructed in the pSPORT-1 plasmid vector (BRL Life Technologies, Inc.). DNA from 44 pools of approximately 5000 colonies each was linearized with Not I and screened by Southern blot, using the rat p55CDC cDNA as a probe. Plaque and colony purification of the clones with the longest inserts was done using standard techniques (63).

Cell Culture, Synchronization and Labelling

HL60 and K562 cells were grown in RPMI1640 (Irvine Scientific, Irvine, Calif.) supplemented with 10 mM HEPES and 15% fetal calf serum. Cells were seeded at a concentration of $0.2 \times 10^6$ cells/ml media. Cells treated with 1 mM sodium butyrate were grown in 75 cm² flasks for three days. Cells induced with phorbol ester were grown in the presence of 30 ng/ml 12-O-teradecanoyl-phorbol 13-acetate (TPA) for three days. Cells were lysed by guanidine thiocyanate and total RNA prepared as described (8). CHOd- cells were maintained in Dulbecco's modified Eagle's medium (DMEM) supplemented with 5% fetal calf serum, glutamine, non-essential amino acids and hypoxanthine. Rat 1 cells were maintained in DMEM containing 10% serum and glutamine and HeLa cells in a Minimum Essential Medium supplemented with 10% serum, glutamine and non-essential amino acids.

HeLa cells were synchronized at the beginning of S phase ($G_1/S$) by the double thymidine/aphidicolin block described by Heintz et al (35). Cells harvested 4 hours later were in S phase (59). Synchronization at the $G_2/M$ transition was achieved by growth in the presence of 0.5 µg/ml nocodazole for a period of 12–14 hours. The media was carefully suctioned off and the non-adherent mitotic cells were harvested by gently pipetting buffer onto the monolayer. The adherent cells were washed with PBS and then lysed. This population is not mitotic and is predominantly in $G_2$ (36).

Asynchronous exponentially growing cells were grown in methionine and cysteine free media containing 2% dialyzed serum for one hour followed by two hours in the same media containing 100 µCi/ml media of $^{35}$S Translabel (ICN Biomedicals, Irvine, Calif.). [$^{32}$P]-orthophosphate (ICN Biomedicals) labelling was performed for 3 hours following a one hour preincubation in phosphate deficient media.

Rat1 cells were growth arrested by rinsing the plates with PBS, followed by rinsing in media containing 0.1% fetal calf serum. The cells were grown in the low serum media for 48 hours to obtain a quiescent population. Labelling with $^{35}$S-TRANSLABEL was performed as described above, with the exception that the dialyzed serum concentration was maintained at 0.1% and the label was incorporated over one hour. For the exponentially growing population of Rat1 cells, the dialyzed serum concentration was maintained at 2% during the course of the labelling.

For flow cytometry analysis, $1 \times 10^6$ cells were washed in PBS and fixed in 70% ethanol, 2.0% Triton X-100 for one hour. Fixed cells were washed in PBS and stained in a solution of 50 µg/ml propidium iodide (PI) and 20 µg/ml RNAse A. The cells were analysed for DNA content (fluorescent intensity) and cell size (forward scatter) using the FACScan (Becton Dickinson, Mountain View, Calif.).

Transfection of CHOd- cells.

A 1.8 kb cDNA obtained from the newborn rat spleen library was cloned into the Bam H1 site of the pMT010/A+ mammalian expression vector (9). The cDNA was inserted downstream of the metallothionein promoter in both the sense (PMIp55s) and antisense (PMTp55as) orientations. These plasmids, as well as vector alone as control, were transfected into cells using Lipofectin (BRL Life Technologies) following the suggested protocol. Initial selection by Geneticin at 400 µg/ml in media without hypoxanthine was followed by stepwise amplification by methotrexate to a final concentration of 2 µM. Growth curves were performed in media containing 0.05 mM zinc to induce the metallothionein promoter.

Antibody Preparation

A p55CDC cDNA clone lacking the first 10 codons was inserted into the EcoR1 site of the pGEX-3X vector (Pharmacia GST gene fusion system). Competent XL-1 cells (Stratagene) were transformed and a colony harboring the recombinant plasmid was isolated. Cultures were induced with isopropyl β-D-thiogalactopyranoside (final concentration 0.1 mM) for growth of the fusion protein. A 76 kDa insoluble fusion protein was obtained which stayed with the pellet following sonication and solubilization with 1% Triton CF-54. The pellet obtained from lysed and sonicated cells was washed twice with PBS containing 1% Triton CF-54 and the resulting pellet extracted with 10M urea. All attempts to extract the fusion protein in anything short of 10M urea failed. The urea extract was dialyzed overnight against PBS and the resulting suspension stored in aliquots at ~80° C. until further purification by SDS-PAGE electrophoresis. The pellets were resuspended in SDS sample buffer and separated in 10% SDS gels. The region between the visible standard markers of 55 kDa and 80 kDa was excised out and the protein recovered by electroelution (Biorad Model 422 ElectroEluter). This preparation was mixed with Freund's complete adjuvant and used for immunization of rabbits. A booster injection was given after four weeks using Freund's incomplete adjuvant. Animals were bled 10–14 days following a booster injection. To obtain an affinity column for purification of antiserum, the crude insoluble fusion protein pellet was resuspended in coupling buffer (0.1M NaHCO3 pH8.3, 0.5M NaCl, 0.5% SDS) and coupled to cyanogen bromide-activated SEPHAROSE, according to the manufacturer's instructions (Pharmacia, Piscataway, N.J.). A coupling efficiency of approximately 0.4 mg protein/ml gel was achieved. The antiserum was first absorbed against an unrelated insoluble fusion protein to remove any antibodies reactive against glutathione S-transferase or contaminating E. coli proteins. This partially purified antiserum was applied to the affinity column. The column was washed with 5× column volumes of PBS and the affinity purified antibodies were eluted with 3M sodium thiocyanate. Pooled antibody fractions were immediately dialyzed against PBS and stored at −80° C. The flowthrough fraction from this column was used as competed antiserum.

Immunoprecipitations And Protein Kinase Assays

In vitro translation was performed using a nuclease treated rabbit reticulocyte lysate (Promega, Madison, Wis.) and [$^3$H]-leucine (Amersham TRK683). The mRNA template was produced by using the Stratagene in vitro transcription kit and the p55CDC cDNA subcloned into the BLUESCRIPT vector as substrate. Cell lysates were prepared as described (59) after rinsing the plates twice with PBS. Cells were lysed in modified radioimmunoprecipitation assay (RIPA) buffer with additional proteases (150 mM NaCl, 1.0% NP-40, 1.0% sodium deoxycholate, 0.1% SDS, 2 mM EDTA, 6 mM $Na_2HPO_4$, 4 mM $NaH_2PO4$ 50 mM NaF, 200 $\mu$M $Na_3VO4$, 20 $\mu$g/ml aprotinin, 1 $\mu$g/ml leupeptin, 10 $\mu$g/ml soybean trypsin inhibitor and 50 $\mu$g/ml phenylmethyl sulfonyl fluoride). All protease inhibitors were purchased from Sigma. Protein concentrations were estimated using the Bicinchoninic acid reagent (Pierce). For 250 $\mu$g lysate in a final volume of 700 $\mu$l RIPA buffer, we used 7 $\mu$l of affinity purified p55CDC antibodies (140 $\mu$g protein/ml) or 12 $\mu$l of p55CDC competed antiserum (700 $\mu$g protein/ml) which gave an equivalent level of immunoglobulin for both preparations. Immunoprecipitation of $p34^{cdc2}$ complexes was done using 10 $\mu$l of the $p_{34}^{cdc2}$ mouse monoclonal antibody 17 (Santa Cruz Biotechnology, Santa Cruz, Calif.). Other antibodies used in this study were Rb(1F8), a mouse monoclonal IgG against a Rb-$\beta$ galactoside fusion protein (Santa Cruz Biotechnology) and Rb(Ab-1), another monoclonal antibody against retinoblastoma protein (Oncogene Science, Uniondale, N.Y.). The immune complexes were routinely incubated overnight on ice and collected next morning with 30 $\mu$l of a 50% slurry of Protein G-SEPHAROSE (Pharmacia). The washed pellets were assayed for histone H1 kinase activity as described in (59). All reactions were performed for 30 minutes at 30°. Assays were also performed using a variety of kinase substrates at the indicated concentrations, using the same assay conditions. Histone H1 was purchased from Boehringer Mannheim while myelin basic protein (MBP), $\beta$- casein and $\alpha$-casein were all purchased from Sigma. The reaction products were quantitated by excising the stained bands from the dried gel and counting.

REFERENCES

1. Amon, A., W. Spevk, I. Muroff, and K. Nasmyth. 1992. Possible involvement of the Cdc20 gene product in microtubule disassembly. Yeast 8:S314.
2. Andersson, L. C., M. Jokinen, and C. G. Gahmberg. 1979. Induction of erythroid differentiation in the human leukaemia cell line K562. Nature 278: 364–365.
3. Beach, D., B. Durkacz, and P. Nurse. 1982. Functionally homologous cell cycle control genes in budding and fission yeast. Nature 300: 706–709.
4. Brizuela, L., G. Draetta, and D. Beach. 1989. Activation of human CDC2 protein as a histone H1 kinase is associated with complex formation with the p62 subunit. Proc. Natl. Acad. Sci. USA 86: 4362–4366.
5. Butler, T. M., A. Ziemiecki, and R. R. Frils. 1990. Megakaryocytic differentiation of K562 cells is associated with changes in the cytoskeletal organization and the pattern of chromatographically distinct forms of phosphotyrosyl-specific protein phosphatases. Cancer Res. 50: 6323–6329. ?
8. Chomczynski, P. and N. Sacchi. 1987. Single-step method of RNA isolation by acid guanidinium thiocyanate-phenol-chloroform extraction. Anal. Biochem. 162: 156–159. ?
11. Crews, C. M., A. Alessandrini, and R. L. Erikson. 1992. Erks: Their fifteen minutes has arrived. Cell Growth Diff. 3: 135–142. ?
13. Deng, X-W., M. Matsui, N. Wei, D. Wagner, A. M. Chu, K. A. Feldmann, and P. H. Quail. 1992. COP1 , an Arabidopsis regulatory gene, encodes a protein with both a zinc-binding motif and a G$\beta$ homologous domain. Cell 71: 791–801. ?
15. Dowdy, S. F., P. W. Hinds, K. Louie, S. I. Reed, A. Arnold, and R. A. Weinberg. 1993. Physical interaction of the retinoblastoma protein with human D cyclins. Cell 73: 499–511.
16. Draetta, G., L. Brizuela, J. Patashkin, and D. Beach. 1987. Identification of p34 and p13, human homologs of the cell cycle regulators of fission yeast encoded by $cdc2^+$ and $suc1^+$. Cell 50: 319–325.
17. Draetta, G. and D. Beach. 1988. Activation of cdc2 protein kinase during mitosis in human cells: Cell cycle-dependent phosphorylation and subunit rearrangement. Cell 54: 17–26.
18. Draetta, G. 1990. Cell cycle control in eukaryotes: molecular mechanisms of cdc2 activation. Trends Biochem. Sci. 15: 378–383.
19. Dulic, V., E. Lees, and S. I. Reed. 1992. Association of human cyclin E with a periodic $G_1$-S phase protein kinase. Science 257: 1958–1961.
20. Dunphy, W. G. and J. W. Newport. 1988. Unravelling of mitotic control mechanisms. Cell 55: 925–928.
21. Dutcher, S. K. and L. H. Hartwell. 1982. The role of S. cerevisiae cell division cycle genes in nuclear fusion. Genetics 100: 175–184.
22. Dynlacht, B. D., R. O. J. Weinzierl, A. Admon, and R. Tjian. 1993. The $dTAF_{11}80$ subunit of Drosophila TF11D contains $\beta$-transducin repeats. Nature. 363:176–179.
23. Erickson, A. K., D. M. Payne, P. A. Martino, A. J., Rossomando, J. Shabanowitz, J. J. Weber, D. F. Hunt, and T. W. Sturgil. 1990. Identification by mass spectrometry of threonine 97 in bovine myelin basic protein as a specific phosphorylation site for mitogen-activated protein kinase. J. Biol. Chem. 265: 19728–19735.
24. Ewen, M. E., B. Faha, E. Marlow, and D. M. Livingston. 1992. Interaction of p107 with cyclin A independent of complex formation with viral oncoproteins. Science 255: 85–87.
25. Ewen, M. E., K. S. Hayla, C. J. Sherr, H. Matsushime, J. Kato, and D. M. Livingston. 1993. Functional interactions of the retinoblastoma protein with mammalian D-type cyclins. Cell 73: 487–497.
26. Fang, F. and J. W. Newport. 1991. Evidence that the $G_1$-S and $G_2$-M transitions are controlled by different cdc2 proteins in higher eukaryotes. Cell 66: 731–742.
27. Fong, H. K. W., J. B. Hurley, R. S. Hopkins, R. Miake-Lye, M. S. Johnson, R. F. Doolittle, and M. I. Simon. 1986. Repetitive segmental structure of the transducin $\beta$ subunit: Homology with the CDC4 gene and identification of related RNAs. Proc. Natl. Acad. Sci. USA 83: 2162–2166.
28. Gautieir, J, Norbury, C., Lohka, M., Nurse, P. and Maller, J. (1988). Purified maturation promoting factor contains the product of a Xenopus homolog of the fission yeast cell cycle control gene $cdc2^+$. Cell 54: 433–439.
29. Girling, R., J. F. Partridge, L. R. Bandara, N. Burden, N. F. Totty, J. J. Hsaun, and N. B. La Thangue. 1993. A new component of the transcription factor DRTF1/E2F. Nature 362: 83–87.
30. Goebl, M. and M. Yanagida. 1991. The TPR snap helix: a novel protein repeat from mitosis to transcription. Trends Biochem. Sci. 16: 173–177.
31. Hanks, S. K., A. M. Quinn, and T. Hunter. 1988. The protein kinase family: Conserved features and deduced phylogeny of the catalytic domains. Science 241: 42–52.
32. Hartwell, L. H. and D. Smith. 1985 Altered fidelity of mitotic chromosome transmission in cell cycle mutants of S. cerevisiae. Genetics 110: 381–395.
33. Hartwell, L. H. 1973. Three additional genes required for deoxyribonucleic acid synthesis in Saccharomyces cerevisiae. J. Bacteriology 115: 966–974.

34. Hartwell, L. H., J. Culotti, J. R. Pringle, and B. J. Reid. 1974. Genetic control of the cell division cycle in yeast. Science 183: 46–51.
35. Heintz, N., H. L. Sive, and R. G. Roeder. 1983. Regulation of human histone gene expression: Kinetics of accumulation and changes in the rate of synthesis and in the half lives of individual histone mRNAs during the HeLa cell cycle. Mol. Cell. Biol. 3: 539–550.
36. Hoffman, I., P. R. Clarke, M. J. Marcote, E. Karsenti, and G. Draetta. 1993. Phosphorylation and activation of human cdc25-C by cdc2-cyclin B and its involvement in the self amplification of MPF at mitosis. EMBO J. 12: 53–63.
37. Kaelin, W. G., W. Krek, W. R. Sellers, J. A. DeCaprio, F. Ajchenbaum, C. S. Fuchs, T. Chittenden, Y. Li, P. J. Farnham, M. A. Blarrar, D. M. Livingston, and E. K. Flemington. 1992. Expression cloning of a cDNA encoding a retinoblastoma-binding protein with E2F-like properties. Cell 70: 351–364.
38. Kochanski, R. S. and G. G. Borisy. 1990. Mode of centriole duplication and distribution. J. Cell Biol. 110: 1599–1605.
39. Koff, A., A. Giordano, D. Desai, K. Yamashita, J. W. Harper, S. Elledge, T. Nishimoto, D. O. Morgan, B. R. Fanza, and J. M. Roberts. 1992. Formation and activation of a cyclin E-cdk2 complex during the G1 phase of the human cell cycle. Science 257: 1689–1694.
40. Labbe, J. C., A. Picard, G. Peaucellieu, J. C. Cavadore, P. Nurse, and M. Doree. 1989. Purification of MPF from starfish: Identification as the H1 histone kinase $p34^{cdc\ 2}$ and a possible mechanism for its periodic activation. Cell 57: 253–263.
41. Langan, T. A., J. Gautier, M. Lohka, R. Hollingsworth, S. Moreno, P. Nurse, J. Maller, and R. A. Sclafani. 1989. Mammalian growth-associated H1 histone kinase: a homolog of $cdc2^+$/CDC28 protein kinases controlling mitotic entry in yeast and frog cells. Mol. Cell. Biol. 9: 3860–3868.
42. Lee, M. G., and P. Nurse. 1987. Complementation used to clone a human homologue of the fission yeast cell cycle control gene cdc2. Nature 327: 31–35.
43. Letwin, K., L. Mizzin, B. Motro, Y. Ben-David, A. Bernstein, and T. Pawson. 1992. A mammalian dual specificity protein kinase, Nek1, is related to the NIMA cell cycle regulator and highly expressed in meiotic germ cells. EMBO. J. 11: 3521–3531.
44. Lew, D. J., V. Dulic, and S. I. Reed. 1991. Isolation of three novel human cyclins by rescue of $G_1$ cyclin (Cln) function in yeast. Cell 66: 1197–1206.
45. Maniotis, A. and M. Schilwa. 1991. Microsurgical removal of centrosomes blocks cell reproduction and centriole generation in BSC-1 cells. Cell 67: 495–504.
46. Matsushime, H., M. E. Ewen, D. K. Strom, J-Y. Kato, S. K. Hanks, M. F. Roussel, and C. J. Sherr. 1992. Identification and properties of an atypical catalytic subunit ($p34^{PSK-J3}$/cdk4) for mammalian D type G1 cyclins. Cell 71: 323–334.
47. Mazia, D. 1987. The chromosome cycle and the centrosome cycle in the mitotic cycle. Int. Rev. Cytol. 100: 49–92.
48. Meyerson, M., G. H. Enders, C-L. Wu, L-K. Su, C. Gorka, C. Nelson, E. Harlow, and L-H. Tsai. 1992. A family of human cdc2 related protein kinases. EMBO J. 11: 2909–2917.
49. Molz, L. and D. Beach. 1993. Characterization of the fission yeast mcs2 cyclin and its associated protein kinase activity. EMBO J. 12: 1723–1732.
50. Nevins, J. R. 1992. E2F: A link between the Rb tumor suppressor protein and viral oncoproteins. Science 258: 424–429.
51. Nurse, P. 1990. Universal control mechanism regulating onset of M-phase. Nature. 344:503–508.
52. O'Farrell, P. H. 1992. Cell cycle control: many ways to skin a cat. Trends. Cell Biol. 2: 159–163.
53. Osmani, S. A., R. T. Pu, and N. R. Morris. 1988. Mitotic induction and maintenance by overexpression of a G2-specific gene that encodes a potential protein kinase. Cell 53: 237–244.
54. Osmani, A. H., K. O. Donnell, R. T. Pu, and S. A. Osmani. 1991. Activation of the nimA protein kinase plays a unique role during mitosis that cannot be bypassed by absence of the bimE checkpoint. EMBO J. 10: 2669–2679.
55. Osmani, A. H., S. L. McGuire, and S. A. Osmani. 1991. Parallel activation of the NIMA and p34cdc2 cell cycle-regulated protein kinases is required to initiate mitosis in A. nidulans. Cell 67: 283–291.
56. Palmer, R. E., M. Koval, and D. Koshland. 1989. The dynamics of chromosome movement in the budding yeast S. cerevisiae. J. Cell Biol. 109: 3355–3366.
57. Paulson, J. C. and K. J. Colley. 1989. Glycosyltransferases. Structure, localization, and control of cell type-specific glycosylation. J. Biol. Chem. 264: 17615–17618.
58. Petersen-Bjorn, S., A. Soltyk, J. D. Beggs, and J. D. Friesen. 1989. Characterization of RNA4/PRP4 from *Saccharomyces cerevisiae:* its gene product is associated with the U4/U6 snRNP. Mol. Cell. Biol. 9: 3698–3709.
59. Pines, J. and T. Hunter. 1989. Isolation of a human cyclin cDNA: Evidence for cyclin mRNA and protein regulation in the cell cycle and for interaction with $p34^{cdc2}$. Cell 58: 833–846.
60. Pines, J. 1993. Cyclins and cyclin-dependent kinases: take your partners. Trends Biochem. Sci. 18: 195–197.
61. Rovera, G., D. Santoli, and C. Damsky. 1979. Human promyelocytic leukemia cells in culture differentiate into macrophage-like cells when treated with a phobol diester. Proc. Natl. Acad. Sci. USA 76: 2779–2783.
62. Ruggieri, R., K. Tanaka, M. Nakafuku, Y. Kaziro, A. Toh-E and K. Matsumoto. 1989 MSI1, a negative regulator of the RAS-cAMP pathway in S. cerevisiae. Proc. Natl. Acad. Sci. USA 86: 8778–8782.
63. Sambrook, J., E. F. Fritsch, and T. Maniatis. 1989. Molecular cloning. A laboratory manual. Second edition.
64. Schweitzer, B. and P. Philippsen. 1991. CDC15, An essential cell cycle gene in *Sacharomyces cerevisiae,* encodes a protein kinase domain. Yeast. 7:265–273.
65. Sethi, N., M. C., Monteagudo, D., Koshland, E., Hogan, and D. J. Burke. 1991 The CDC20 gene product of *Saccharomyces cerevisiae,* a β-transducin homolog, is required for a subset of microtubule-dependent cellular processes. Mol. Cell. Biol. 11: 5592–5602.
66. Shaw, D. R., H. Richter, R. Giorda, T. Ohmachi, and H. L. Ennis. 1989. Nucleotide sequences of D. discoideum developmentally regulated cDNAs rich in (AAC) imply proteins that contain clusters of asparagine, glutamine, or threonine. Mol. Gen. Genet. 218: 453–459.
67. Sherr, C. J. 1993. Mammalian G1 cyclins. Cell 73: 1059–1065.
68. Simchen, G. and J. Hirschberg. 1977. Effects of the mitotic cell cycle mutation CDC4 on yeast meiosis. Genetics 86: 57–72.
69. Spevak, W., B. D. Keiper, C. Stratowa, and M. J. Castanon. 1993. Saccharomyces cerevisiae cdc15 mutants arrested at a late stage in anaphase are rescued by Xenopus cDNAs encoding N-ras or a protein with β-transducin repeats. Mol. Cell. Biol. 13:4953–4966.
70. Turner, A. M., K. M. Zsebo, F. Martin, F. W. Jacobsen, L. G. Bennet, and V. C. Broudy. 1992. Non-hematopoietic tumor cell lines express stem cell factor and display c-kit receptors. Blood 80: 374–381.
71. Vallen, E. A., T. Y. Scherson, T. Roberts, K. V. Zee, and M. D. Rose. 1993. Asymmetric mitotic segregation of the yeast spindle pole body. Cell 69: 505–515.
72. Van der Voorn, L. and H. L. Ploegh. 1992. The WD-40 repeat. FEBS Lett. 307:131–134.
73. Weinstein, J., E. U. Lee, K. McEntee, P-H. Lai, and J. C. Paulson. 1987. Primary structure of β-galactoside a 2,6-sialyltransferase. J. Biol. Chem. 262: 17735–17743.
75. Winey, M., and B. Byers. 1992. Spindle pole body of *S. cerevisiae*: A model for genetic analysis of the centrosome cycle. The Centrosome. V. Kalnius ed. (Orlando: Academic Press). pp201–222.
76. Wittenberg, C. and S. I. Reed. 1989. Conservation of function and regulation within the cdc28/cdc2 protein kinase family: Characterization of the human cdc2Hs protein kinase in *Saccharomyces cerevisiae*. Mol. Cell. Biol. 9: 4064–4068.
77. Yochem, J. and B. Byers. 1987. Structural comparison of the yeast cell division cycle gene CDC4 and a related pseudogene. J. Mol. Biol. 195: 233–245.
78. Zhang, M., L. S. Rosenblum-Vos, C. U. Lowry, K. A. Boakye, and R. S. Zitomer. 1991. A yeast protein with homology to the β-subunit of G proteins is involved in control of heme-regulated and catabolite-repressed genes. Gene 97: 153–161.

While the present invention has been described in terms of the preferred embodiments, it is understood that variations and modifications will occur to those skilled in the art. Therefore, it is intended that the appended claims cover all such equivalent variations which come within the scope of the invention as claimed.

What is claimed is:

1. An isolated mammalian p55CDC polypeptide capable of forming a complex having cell cycle dependent kinase activity against at least histone H1, alpha-casein, and myelin basic protein comprising the amino acid sequence of SEQ ID NO: 4 or a biologically active fragment thereof.

2. A polypeptide of claim 1, wherein said polypeptide is the product of procaryotic or eucaryotic expression of an exogenous DNA sequence.

3. A polypeptide of claim 1 comprising SEQ ID NO: 4.

4. An isolated mammalian p55CDC polypeptide capable of forming a complex having cell cycle dependent kinase activity against at least histone H1, alpha-casein, and myelin basic protein comprising the amino acid sequence of SEQ ID NO:2 or a biologically active fragment thereof.

5. A polypeptide of claim 4, wherein said polypeptide is the product of procaryotic or eucaryotic expression of an exogenous sequence.

6. A polypeptide of claim 4, comprising SEQ ID NO: 2.

7. A biologically active polypeptide which is about 95% homologous to the polypeptide of claim 3 or 6.

* * * * *

UNITED STATES PATENT AND TRADEMARK OFFICE
CERTIFICATE OF CORRECTION

PATENT NO. : 6,291,642 B1
DATED : September 19, 2001
INVENTOR(S) : Jasminder Weinstein Page 1 of 1

It is certified that error appears in the above-identified patent and that said Letters Patent is hereby corrected as shown below:

Column 1,
Line 8, remove "Background of the Invention"

Column 3,
Line 65, change "β-repeats" to -- Gβ-repeats --.

Column 7,
Line 65, change "GE" to -- Gβ --.

Column 9,
Line 53, change "D55CDC" to -- p55CDC --.

Column 16,
Line 51, change "Sequenase" to -- SEQUENASE --.
Line 53, change "SEQUENCING" to -- Sequencing --.
Line 59, change "D55CDC" to -- p55CDC --.

Column 19,
Line 16, change "$p_{34}^{cdc2}$" to -- $p34^{cdc2}$ --.

Signed and Sealed this

Thirtieth Day of April, 2002

Attest:

JAMES E. ROGAN
*Attesting Officer*   *Director of the United States Patent and Trademark Office*

SEQUENCE LISTING

```
<160> NUMBER OF SEQ ID NOS: 31

<210> SEQ ID NO 1
<211> LENGTH: 1767
<212> TYPE: DNA
<213> ORGANISM: Rattus sp.

<400> SEQUENCE: 1
ggcgtgcctt tagccggtca gaaaagaacg cattcggcac ttctacagac gcactgagga      60
gtcagggatt tgtgtttggg agaggtttac gaagaggtgc tgggctggtg cgaactgtgg     120
caggcagagc ccaggagtcc tgcgaggtcc tgagtttggt cgcctctcac ccccctcccc     180
ggtagacggg ccatggcgca gttcgtgttc gagagcgatt tgcattcact gcttcaactg     240
gacgcgccca tccccaatgc accgattgct cgctggcagc gcaaagcaaa agaagccaca     300
ggcccagccc cctcgcctat gcgggccgcc aacagatcac acagcgccgg tcggaccccg     360
ggccgaactc ctggcaaatc taattctaag gttcagacca cccctagcaa acctggaggt     420
gagcgctata tcccccaacg tagtgcttcc caaatggagg tggccagctt cctcttgagc     480
aaggagaacc agccggaaga cggggtacg cccaccaaga aggagcatca gaaagcctgg     540
gctcggaacc tgaacggttt tgatgtggag gaagccaaga tcctcaggct cagtggaaaa     600
cctcagaatg ccccagaagg ctaccagaac agattgaaag tactctacag ccagaaagcc     660
acgcctggct ccagtcggaa ggcttgcaga tacattcctt ccctgccaga caggattctt     720
gatgcccctg aaatccggaa tgactactac ctgaatcttg tcgattggag ctctggaaat     780
gtattagctg tggcactgga caacagtgtg tacttatgga acgctggttc cggtgacatc     840
ctgcagctgt tgcaaatgga gcagcctggg gactacatat catccgtggc ctggatcaaa     900
gagggcaact acctggctgt gggcaccagt aatgctgagg tgcagctatg ggatgtgcag     960
cagcagaaac ggcttcgaaa catgaccagc cactctgctc gagtaagctc cctgagttgg    1020
aacagctata tcctgtcaag tggttcacga tctgccaca tccaccacca cgatgttcga    1080
gtagcagaac accatgtggc cacactgagt ggccatagcc aggaagtatg tgggctgcgc    1140 tgggcccag atggacgaca tctggcaagc ggtggcaatg ataacattgt caacgtgtgg    1200
cctagtggtc ctggagaaag tggctgggtt cccctgcaga cattcactca acatcaaggt    1260
gctgtcaagg ctgttgcatg gtgtccctgg cagtccaata tcctggcaac aggaggaggt    1320
```

```
accagtgacc gacacattcg catttggaac gtctgctctg gagcctgtct gagtgctgtg    1380
gatgtgcatt cccaggtgtg ctccatcctc tggtctcccc actataagga gctcatctca    1440
ggccatggct ttgcccagaa ccagctggtt atttggaagt acccaaccat ggccaaggtg    1500
gcagagctca aggtcacac agcccgggtc ctgagtctca ccatgagtcc agacggggcc     1560
acagtggcat ctgcagcagc cgatgagact ctgcggctct ggcgctgctt tgagctggac    1620 cctgccttc ggcgggagcg ggaaaaagcc agcacatcta aaagtagcct catccaccaa     1680
ggcatccggt gaaagacaac cctttctttt cccttcttga ttttgttgtt gtttattttt    1740
ttctaataaa gttcatatct tcctttc                                        1767
```

<210> SEQ ID NO 2
<211> LENGTH: 499
<212> TYPE: PRT
<213> ORGANISM: Rattus sp.

<400> SEQUENCE: 2

```
Met Ala Gln Phe Val Phe Glu Ser Asp Leu His Ser Leu Leu Gln Leu
  1               5                  10                  15

Asp Ala Pro Ile Pro Asn Ala Pro Ile Ala Arg Trp Gln Arg Lys Ala
             20                  25                  30

Lys Glu Ala Thr Gly Pro Ala Pro Ser Pro Met Arg Ala Ala Asn Arg
         35                  40                  45

Ser His Ser Ala Gly Arg Thr Pro Gly Arg Thr Pro Gly Lys Ser Asn
     50                  55                  60

Ser Lys Val Gln Thr Thr Pro Ser Lys Pro Gly Gly Glu Arg Tyr Ile
 65                  70                  75                  80

Pro Gln Arg Ser Ala Ser Gln Met Glu Val Ala Ser Phe Leu Leu Ser
                 85                  90                  95

Lys Glu Asn Gln Pro Glu Asp Gly Gly Thr Pro Thr Lys Lys Glu His
            100                 105                 110

Gln Lys Ala Trp Ala Arg Asn Leu Asn Gly Phe Asp Val Glu Glu Ala
        115                 120                 125

Lys Ile Leu Arg Leu Ser Gly Lys Pro Gln Asn Ala Pro Glu Gly Tyr
    130                 135                 140

Gln Asn Arg Leu Lys Val Leu Tyr Ser Gln Lys Ala Thr Pro Gly Ser
145                 150                 155                 160

Ser Arg Lys Ala Cys Arg Tyr Ile Pro Ser Leu Pro Asp Arg Ile Leu
                165                 170                 175

Asp Ala Pro Glu Ile Arg Asn Asp Tyr Tyr Leu Asn Leu Val Asp Trp
            180                 185                 190

Ser Ser Gly Asn Val Leu Ala Val Ala Leu Asp Asn Ser Val Tyr Leu
        195                 200                 205

Trp Asn Ala Gly Ser Gly Asp Ile Leu Gln Leu Leu Gln Met Glu Gln
    210                 215                 220

Pro Gly Asp Tyr Ile Ser Ser Val Ala Trp Ile Lys Glu Gly Asn Tyr
225                 230                 235                 240

Leu Ala Val Gly Thr Ser Asn Ala Glu Val Gln Leu Trp Asp Val Gln
                245                 250                 255

Gln Gln Lys Arg Leu Arg Asn Met Thr Ser His Ser Ala Arg Val Ser
            260                 265                 270

Ser Leu Ser Trp Asn Ser Tyr Ile Leu Ser Ser Gly Ser Arg Ser Gly
        275                 280                 285
```

```
His Ile His His Asp Val Arg Val Ala Glu His His Val Ala Thr
            290                 295                 300
Leu Ser Gly His Ser Gln Glu Val Cys Gly Leu Arg Trp Ala Pro Asp
305                 310                 315                 320
Gly Arg His Leu Ala Ser Gly Gly Asn Asp Asn Ile Val Asn Val Trp
                    325                 330                 335
Pro Ser Gly Pro Gly Glu Ser Gly Trp Val Pro Leu Gln Thr Phe Thr
                340                 345                 350
Gln His Gln Gly Ala Val Lys Ala Val Ala Trp Cys Pro Trp Gln Ser
            355                 360                 365
Asn Ile Leu Ala Thr Gly Gly Thr Ser Asp Arg His Ile Arg Ile
        370                 375                 380
Trp Asn Val Cys Ser Gly Ala Cys Leu Ser Ala Val Asp Val His Ser
385                 390                 395                 400
Gln Val Cys Ser Ile Leu Trp Ser Pro His Tyr Lys Glu Leu Ile Ser
                    405                 410                 415
Gly His Gly Phe Ala Gln Asn Gln Leu Val Ile Trp Lys Tyr Pro Thr
                420                 425                 430
Met Ala Lys Val Ala Glu Leu Lys Gly His Thr Ala Arg Val Leu Ser
            435                 440                 445
Leu Thr Met Ser Pro Asp Gly Ala Thr Val Ala Ser Ala Ala Ala Asp
        450                 455                 460
Glu Thr Leu Arg Leu Trp Arg Cys Phe Glu Leu Asp Pro Ala Leu Arg
465                 470                 475                 480
Arg Glu Arg Glu Lys Ala Ser Thr Ser Lys Ser Ser Leu Ile His Gln
                    485                 490                 495
Gly Ile Arg

<210> SEQ ID NO 3
<211> LENGTH: 1700
<212> TYPE: DNA
<213> ORGANISM: Homo sapiens

<400> SEQUENCE: 3
gtcgacccac gcgtccgggc gtaagccagg cgtgttaaag ccggtcggaa ctgctccgga      60
gggcacgggc tccgtaggca ccaactgcaa ggacccctcc ccctgcgggc gctcccatgg     120
cacagttcgc gttcgagagt gacctgcact cgctgcttca gctggatgca cccatcccca     180
atgcaccccc tgcgcgctgg cagcgcaaag ccaaggaagc gcaggcccg gccccctcac     240
ccatgcgggc cgccaaccga tcccacagcc ccggcaggac tccgggccga actcctggca     300
aatccagttc caaggttcag accactccta gcaaacctgg cggtgaccgc tatatccccc     360
atcgcagtgc tgcccagatg gaggtggcca gcttcctcct gagcaaggag aaccagtctg     420
aaacagcca cgcccacc aagaaggaac atcagaaagc tgggctttg aacctgaacg     480
gttttgatgt agaggaagcc aagatccttc ggctcagtgg aaaaccacaa atgcgccag     540
agggttatca gaacagactg aaagtactct acagccaaaa ggccactcct ggctccagcc     600
ggaagacctg ccgttacatt ccttccctgc cagaccgtat cctggatgcg cctgaaatcc     660
gaaatgacta ttacctgaac cttgtggatt ggagttctgg gaatgtactg gccgtggcac     720
tggacaacag tgtgtacctg tggagtgcaa gctctggtga catcctgcag cttttgcaaa     780
tggagcagcc tggggaatat atatcctctg tggcctggat caaagagggc aactacttgg     840
ctgtgggcac cagcagtgct gaggtgcagc tatgggatgt gcagcagcag aaacggcttc     900
```

-continued

```
gaaatatgac cagtcactct gcccgagtgg gctccctaag ctggaacagc tatatcctgt     960
ccagtggttc acgttctggc cacatccacc accatgatgt tcgggtagca gaacaccatg    1020
tggccacact gagtggccac agccaggaag tgtgtgggct cgctgggcc ccagatggac     1080
gacatttggc cagtggtggt aatgataact tggtcaatgt gtggcctagt gctcctggag    1140
agggtggctg ggttcctctg cagacattca cccagcatca agggctgtc aaggccgtag     1200
catggtgtcc ctggcagtcc aatgtcctgg caacaggagg gggcaccagt gatcgacaca    1260
ttcgcatctg gaatgtgtgc tctggggcct gtctgagtgc cgtggatgcc cattcccagg    1320
tgtgctccat cctctggtct ccccattaca aggagctcat ctcaggccat ggctttgcac    1380
agaaccagct agttatttgg aagtacccaa ccatggccaa ggtggctgaa ctcaaaggtc    1440
acacatcccg ggtcctgagt ctgaccatga gcccagatgg ggccacagtg gcatccgcag    1500
cagcagatga gaccctgagg ctatggcgct gttttgagtt ggaccctgcg cggcggcggg    1560
agcgggagaa ggccagtgca gccaaaagca gcctcatcca ccaaggcatc cgctgaagac    1620
caacccatca cctcagttgt tttttatttt tctaataaag tcatgtctcc cttcatgttt    1680
ttttttttaa aaaaaaaaa                                                 1700
```

<210> SEQ ID NO 4
<211> LENGTH: 499
<212> TYPE: PRT
<213> ORGANISM: Homo sapiens

<400> SEQUENCE: 4

```
Met Ala Gln Phe Ala Phe Glu Ser Asp Leu His Ser Leu Leu Gln Leu
  1               5                  10                  15

Asp Ala Pro Ile Pro Asn Ala Pro Ala Arg Trp Gln Arg Lys Ala
             20                  25                  30

Lys Glu Ala Ala Gly Pro Ala Pro Ser Pro Met Arg Ala Ala Asn Arg
         35                  40                  45

Ser His Ser Ala Gly Arg Thr Pro Gly Arg Thr Pro Gly Lys Ser Ser
     50                  55                  60

Ser Lys Val Gln Thr Thr Pro Ser Lys Pro Gly Gly Asp Arg Tyr Ile
 65                  70                  75                  80

Pro His Arg Ser Ala Ala Gln Met Glu Val Ala Ser Phe Leu Leu Ser
                 85                  90                  95

Lys Glu Asn Gln Ser Glu Asn Ser Gln Thr Pro Thr Lys Lys Glu His
            100                 105                 110

Gln Lys Ala Trp Ala Leu Asn Leu Asn Gly Phe Asp Val Glu Glu Ala
        115                 120                 125

Lys Ile Leu Arg Leu Ser Gly Lys Pro Gln Asn Ala Pro Glu Gly Tyr
    130                 135                 140

Gln Asn Arg Leu Lys Val Leu Tyr Ser Gln Lys Ala Thr Pro Gly Ser
145                 150                 155                 160

Ser Arg Lys Thr Cys Arg Tyr Ile Pro Ser Leu Pro Asp Arg Ile Leu
                165                 170                 175

Asp Ala Pro Glu Ile Arg Asn Asp Tyr Tyr Leu Asn Leu Val Asp Trp
            180                 185                 190

Ser Ser Gly Asn Val Leu Ala Val Ala Leu Asp Asn Ser Val Tyr Leu
        195                 200                 205

Trp Ser Ala Ser Ser Gly Asp Ile Leu Gln Leu Leu Gln Met Glu Gln
    210                 215                 220

Pro Gly Glu Tyr Ile Ser Ser Val Ala Trp Ile Lys Glu Gly Asn Tyr
```

-continued

```
            225                 230                 235                 240
Leu Ala Val Gly Thr Ser Ser Ala Glu Val Gln Leu Trp Asp Val Gln
                245                 250                 255
Gln Gln Lys Arg Leu Arg Asn Met Thr Ser His Ser Ala Arg Val Gly
            260                 265                 270
Ser Leu Ser Trp Asn Ser Tyr Ile Leu Ser Ser Gly Ser Arg Ser Gly
        275                 280                 285
His Ile His His His Asp Val Arg Val Ala Glu His His Val Ala Thr
    290                 295                 300
Leu Ser Gly His Ser Gln Glu Val Cys Gly Leu Arg Trp Ala Pro Asp
305                 310                 315                 320
Gly Arg His Leu Ala Ser Gly Gly Asn Asp Asn Leu Val Asn Val Trp
                325                 330                 335
Pro Ser Ala Pro Gly Glu Gly Gly Trp Val Pro Leu Gln Thr Phe Thr
            340                 345                 350
Gln His Gln Gly Ala Val Lys Ala Val Ala Trp Cys Pro Trp Gln Ser
        355                 360                 365
Asn Val Leu Ala Thr Gly Gly Gly Thr Ser Asp Arg His Ile Arg Ile
    370                 375                 380
Trp Asn Val Cys Ser Gly Ala Cys Leu Ser Ala Val Asp Ala His Ser
385                 390                 395                 400
Gln Val Cys Ser Ile Leu Trp Ser Pro His Tyr Lys Glu Leu Ile Ser
                405                 410                 415
Gly His Gly Phe Ala Gln Asn Gln Leu Val Ile Trp Lys Tyr Pro Thr
            420                 425                 430
Met Ala Lys Val Ala Glu Leu Lys Gly His Thr Ser Arg Val Leu Ser
        435                 440                 445
Leu Thr Met Ser Pro Asp Gly Ala Thr Val Ala Ser Ala Ala Ala Asp
    450                 455                 460
Glu Thr Leu Arg Leu Trp Arg Cys Phe Glu Leu Asp Pro Ala Arg Arg
465                 470                 475                 480
Arg Glu Arg Glu Lys Ala Ser Ala Ala Lys Ser Ser Leu Ile His Gln
                485                 490                 495
Gly Ile Arg

<210> SEQ ID NO 5
<211> LENGTH: 43
<212> TYPE: PRT
<213> ORGANISM: Rattus sp.

<400> SEQUENCE: 5

Ile Pro Ser Leu Pro Asp Arg Ile Leu Asp Ala Pro Glu Ile Arg Asn
 1               5                  10                  15
Asp Tyr Tyr Leu Asn Leu Val Asp Trp Ser Ser Gly Asn Val Leu Ala
            20                  25                  30
Val Ala Leu Asp Asn Ser Val Tyr Leu Trp Asn
        35                  40

<210> SEQ ID NO 6
<211> LENGTH: 44
<212> TYPE: PRT
<213> ORGANISM: Rattus sp.

<400> SEQUENCE: 6

Ala Gly Ser Gly Asp Ile Leu Gln Leu Leu Gln Met Glu Gln Pro Gly
 1               5                  10                  15
```

```
Asp Tyr Ile Ser Ser Val Ala Trp Ile Lys Glu Gly Asn Tyr Leu Ala
            20                  25                  30

Val Gly Thr Ser Asn Ala Glu Val Gln Leu Trp Asp
        35                  40

<210> SEQ ID NO 7
<211> LENGTH: 40
<212> TYPE: PRT
<213> ORGANISM: Rattus sp.

<400> SEQUENCE: 7

Val Gln Gln Gln Lys Arg Leu Arg Asn Met Thr Ser His Ser Ala Arg
  1               5                  10                  15

Val Ser Ser Leu Ser Trp Asn Ser Tyr Ile Leu Ser Ser Gly Ser Arg
            20                  25                  30

Ser Gly His Ile His His His Asp
        35                  40

<210> SEQ ID NO 8
<211> LENGTH: 43
<212> TYPE: PRT
<213> ORGANISM: Rattus sp.

<400> SEQUENCE: 8

Val Arg Val Ala Glu His His Val Ala Thr Leu Ser Gly His Ser Gln
  1               5                  10                  15

Glu Val Cys Gly Leu Arg Trp Ala Pro Asp Gly Arg His Leu Ala Ser
            20                  25                  30

Gly Gly Asn Asp Asn Ile Val Asn Val Trp Pro
        35                  40

<210> SEQ ID NO 9
<211> LENGTH: 49
<212> TYPE: PRT
<213> ORGANISM: Rattus sp.

<400> SEQUENCE: 9

Ser Gly Pro Gly Glu Ser Gly Trp Val Pro Leu Gln Thr Phe Thr Gln
  1               5                  10                  15

His Gln Gly Ala Val Lys Ala Val Ala Trp Cys Pro Trp Gln Ser Asn
            20                  25                  30

Ile Leu Ala Thr Gly Gly Gly Thr Ser Asp Arg His Ile Arg Ile Trp
        35                  40                  45

Asn

<210> SEQ ID NO 10
<211> LENGTH: 43
<212> TYPE: PRT
<213> ORGANISM: Rattus sp.

<400> SEQUENCE: 10

Val Cys Ser Gly Ala Cys Leu Ser Ala Val Asp Val His Ser Gln Val
  1               5                  10                  15

Cys Ser Ile Leu Trp Ser Pro His Tyr Lys Glu Leu Ile Ser Gly His
            20                  25                  30

Gly Phe Ala Gln Asn Gln Leu Val Ile Trp Lys
        35                  40

<210> SEQ ID NO 11
```

```
<211> LENGTH: 42
<212> TYPE: PRT
<213> ORGANISM: Rattus sp.

<400> SEQUENCE: 11

Tyr Pro Thr Met Ala Lys Val Ala Glu Leu Lys Gly His Thr Ala Arg
 1               5                  10                  15

Val Leu Ser Leu Thr Met Ser Pro Asp Gly Ala Thr Val Ala Ser Ala
            20                  25                  30

Ala Ala Asp Glu Thr Leu Arg Leu Trp Arg
        35                  40

<210> SEQ ID NO 12
<211> LENGTH: 39
<212> TYPE: PRT
<213> ORGANISM: Saccharomyces cerevisiae

<400> SEQUENCE: 12

Pro Glu Arg Ile Leu Asp Ala Pro Gly Phe Gln Asp Asp Phe Tyr Leu
 1               5                  10                  15

Asn Leu Leu Ser Trp Ser Lys Lys Asn Val Leu Ala Ile Ala Leu Asp
            20                  25                  30

Thr Ala Leu Tyr Leu Trp Asn
        35

<210> SEQ ID NO 13
<211> LENGTH: 40
<212> TYPE: PRT
<213> ORGANISM: Homo sapiens

<400> SEQUENCE: 13

Leu Pro Asp Arg Ile Leu Asp Ala Pro Glu Ile Arg Asn Asp Tyr Tyr
 1               5                  10                  15

Leu Asn Leu Val Asp Trp Ser Ser Gly Asn Val Leu Ala Val Ala Leu
            20                  25                  30

Asp Asn Ser Val Tyr Leu Trp Ser
        35                  40

<210> SEQ ID NO 14
<211> LENGTH: 52
<212> TYPE: PRT
<213> ORGANISM: Saccharomyces cerevisiae

<400> SEQUENCE: 14

Leu Ser Asp Glu Ile Phe Ser Ala Ile Asn Asn Asn Leu Pro His Ala
 1               5                  10                  15

Tyr Phe Lys Asn Leu Leu Phe Arg Leu Val Ala Asn Met Asp Arg Ser
            20                  25                  30

Glu Leu Ser Asp Leu Gly Thr Leu Ile Lys Asp Asn Leu Lys Arg Asp
        35                  40                  45

Leu Ile Thr Ser
        50

<210> SEQ ID NO 15
<211> LENGTH: 42
<212> TYPE: PRT
<213> ORGANISM: Saccharomyces cerevisiae

<400> SEQUENCE: 15

Ala Thr Thr Gly Asp Val Ser Leu Leu Thr Asp Phe Glu Asn Thr Thr
 1               5                  10                  15
```

```
Ile Cys Ser Val Thr Trp Ser Asp Asp Cys His Ile Ser Met Ala
                20                  25                  30

Lys Glu Asp Gly Asn Thr Glu Ile Trp Asp
         35                  40
```

<210> SEQ ID NO 16
<211> LENGTH: 44
<212> TYPE: PRT
<213> ORGANISM: Homo sapiens

<400> SEQUENCE: 16

```
Ala Ser Ser Gly Asp Ile Leu Gln Leu Gln Met Glu Gln Pro Gly
 1               5                  10                  15

Glu Tyr Ile Ser Ser Val Ala Trp Ile Lys Glu Gly Asn Tyr Leu Ala
                20                  25                  30

Val Gly Thr Ser Ser Ala Glu Val Gln Leu Trp Asp
         35                  40
```

<210> SEQ ID NO 17
<211> LENGTH: 67
<212> TYPE: PRT
<213> ORGANISM: Saccharomyces cerevisiae

<400> SEQUENCE: 17

```
Leu Pro Phe Glu Ile Ser Leu Lys Ile Phe Asn Tyr Leu Gln Phe Glu
 1               5                  10                  15

Asp Ile Ile Asn Ser Leu Gly Val Ser Gln Asn Trp Asn Lys Ile Ile
                20                  25                  30

Arg Lys Ser Thr Ser Leu Trp Lys Lys Leu Leu Ile Ser Glu Asn Phe
         35                  40                  45

Val Ser Pro Lys Gly Phe Asn Ser Leu Asn Leu Lys Leu Ser Gln Lys
     50                  55                  60

Tyr Pro Lys
 65
```

<210> SEQ ID NO 18
<211> LENGTH: 41
<212> TYPE: PRT
<213> ORGANISM: Saccharomyces cerevisiae

<400> SEQUENCE: 18

```
Val Glu Thr Met Ser Leu Ile Arg Thr Met Arg Ser Gly Leu Gly Val
 1               5                  10                  15

Arg Ile Gly Ser Leu Ser Trp Leu Asp Thr Leu Ile Ala Thr Gly Ser
                20                  25                  30

Arg Ser Gly Glu Ile Gln Ile Asn Asp
         35                  40
```

<210> SEQ ID NO 19
<211> LENGTH: 40
<212> TYPE: PRT
<213> ORGANISM: Homo sapiens

<400> SEQUENCE: 19

```
Val Gln Gln Gln Lys Arg Leu Arg Asn Met Thr Ser His Ser Ala Arg
 1               5                  10                  15

Val Gly Ser Leu Ser Trp Asn Ser Tyr Ile Leu Ser Gly Ser Arg
                20                  25                  30

Ser Gly His Ile His His His Asp
```

<210> SEQ ID NO 20
<211> LENGTH: 64
<212> TYPE: PRT
<213> ORGANISM: Saccharomyces cerevisiae

<400> SEQUENCE: 20

Leu Ser Gln Gln Asp Arg Leu Arg Leu Ser Phe Leu Glu Asn Ile Phe
 1               5                  10                  15

Ile Leu Lys Asn Trp Tyr Asn Pro Lys Phe Val Pro Gln Arg Thr Thr
            20                  25                  30

Leu Arg Gly His Met Thr Ser Val Ile Thr Cys Leu Gln Phe Glu Asp
        35                  40                  45

Asn Tyr Val Ile Thr Gly Ala Asp Asp Lys Met Ile Arg Val Tyr Asp
    50                  55                  60

<210> SEQ ID NO 21
<211> LENGTH: 43
<212> TYPE: PRT
<213> ORGANISM: Saccharomyces cerevisiae

<400> SEQUENCE: 21

Val Arg Ile Lys Gln His Ile Val Ser Thr Trp Ala Glu His Thr Gly
 1               5                  10                  15

Glu Val Cys Gly Leu Ser Tyr Lys Ser Asp Gly Leu Gln Leu Ala Ser
            20                  25                  30

Gly Gly Asn Asp Asn Thr Val Met Ile Trp Asp
        35                  40

<210> SEQ ID NO 22
<211> LENGTH: 43
<212> TYPE: PRT
<213> ORGANISM: Homo sapiens

<400> SEQUENCE: 22

Val Arg Val Ala Glu His His Val Ala Thr Leu Ser Gly His Ser Gln
 1               5                  10                  15

Glu Val Cys Gly Leu Arg Trp Ala Pro Asp Gly Arg His Leu Ala Ser
            20                  25                  30

Gly Gly Asn Asp Asn Leu Val Asn Val Trp Pro
        35                  40

<210> SEQ ID NO 23
<211> LENGTH: 41
<212> TYPE: PRT
<213> ORGANISM: Saccharomyces cerevisiae

<400> SEQUENCE: 23

Ser Ile Asn Lys Lys Phe Leu Leu Gln Leu Ser Gly His Asp Gly Gly
 1               5                  10                  15

Val Trp Ala Leu Lys Tyr Ala His Gly Gly Ile Leu Val Ser Gly Ser
            20                  25                  30

Thr Asp Arg Thr Val Arg Val Trp Asp
        35                  40

<210> SEQ ID NO 24
<211> LENGTH: 45
<212> TYPE: PRT
<213> ORGANISM: Saccharomyces cerevisiae

```
<400> SEQUENCE: 24

Thr Arg Thr Ser Leu Pro Gln Phe Ser Lys Lys Thr His Thr Ala Ala
 1               5                  10                  15

Val Lys Ala Leu Ser Trp Cys Pro Tyr Ser Pro Asn Ile Asn Asn Ser
            20                  25                  30

Gly Gly Gly Gln Thr Asp Lys His Ile His Phe Trp Asn
        35                  40                  45

<210> SEQ ID NO 25
<211> LENGTH: 49
<212> TYPE: PRT
<213> ORGANISM: Homo sapiens

<400> SEQUENCE: 25

Ser Ala Pro Gly Glu Gly Gly Trp Val Pro Leu Gln Thr Phe Thr Gln
 1               5                  10                  15

His Gln Gly Ala Val Lys Ala Val Ala Trp Cys Pro Trp Gln Ser Asn
            20                  25                  30

Val Leu Ala Thr Gly Gly Gly Thr Ser Asp Arg His Ile Arg Ile Trp
        35                  40                  45

Asn

<210> SEQ ID NO 26
<211> LENGTH: 44
<212> TYPE: PRT
<213> ORGANISM: Saccharomyces cerevisiae

<400> SEQUENCE: 26

Ile Lys Lys Gly Cys Cys Thr His Val Phe Glu Gly His Asn Ser Thr
 1               5                  10                  15

Val Arg Cys Leu Asp Ile Val Glu Tyr Lys Asn Ile Lys Tyr Ile Val
            20                  25                  30

Thr Gly Ser Arg Asp Asn Thr Leu His Val Trp Lys
        35                  40

<210> SEQ ID NO 27
<211> LENGTH: 21
<212> TYPE: PRT
<213> ORGANISM: Saccharomyces cerevisiae

<400> SEQUENCE: 27

Ser Ile Thr Gly Ala Arg Val Gly Ser Ile Asn Thr Gly Ser Gln Val
 1               5                  10                  15

Ser Ser Leu His Trp
            20

<210> SEQ ID NO 28
<211> LENGTH: 43
<212> TYPE: PRT
<213> ORGANISM: Homo sapiens

<400> SEQUENCE: 28

Val Cys Ser Gly Ala Cys Leu Ser Ala Val Asp Ala His Ser Gln Val
 1               5                  10                  15

Cys Ser Ile Leu Trp Ser Pro His Tyr Lys Glu Leu Ile Ser Gly His
            20                  25                  30

Gly Phe Ala Gln Asn Gln Leu Val Ile Trp Lys
        35                  40
```

```
<210> SEQ ID NO 29
<211> LENGTH: 63
<212> TYPE: PRT
<213> ORGANISM: Saccharomyces cerevisiae

<400> SEQUENCE: 29

Leu Pro Lys Glu Ser Ser Val Pro Asp His Gly Glu Glu His Asp Tyr
  1               5                  10                  15

Pro Leu Val Phe His Thr Pro Glu Glu Asn Pro Tyr Phe Val Gly Val
             20                  25                  30

Leu Arg Gly His Met Ala Ser Val Arg Thr Val Ser Gly His Gly Asn
         35                  40                  45

Ile Val Val Ser Gly Ser Tyr Asp Asn Thr Leu Ile Val Trp Asp
     50                  55                  60

<210> SEQ ID NO 30
<211> LENGTH: 42
<212> TYPE: PRT
<213> ORGANISM: Homo sapiens

<400> SEQUENCE: 30

Tyr Pro Thr Met Ala Lys Val Ala Glu Leu Lys Gly His Thr Ser Arg
  1               5                  10                  15

Val Leu Ser Leu Thr Met Ser Pro Asp Gly Ala Thr Val Ala Ser Ala
             20                  25                  30

Ala Ala Asp Glu Thr Leu Arg Leu Trp Arg
         35                  40

<210> SEQ ID NO 31
<211> LENGTH: 42
<212> TYPE: PRT
<213> ORGANISM: Saccharomyces cerevisiae

<400> SEQUENCE: 31

Val Ala Gln Met Lys Cys Leu Tyr Ile Leu Ser Gly His Thr Asp Arg
  1               5                  10                  15

Ile Tyr Ser Thr Ile Tyr Asp His Glu Arg Lys Arg Cys Ile Ser Ala
             20                  25                  30

Ser Met Asp Thr Thr Ile Arg Ile Trp Asp
         35                  40
```